US007754426B2

(12) United States Patent
Somasundaram et al.

(10) Patent No.: US 7,754,426 B2
(45) Date of Patent: Jul. 13, 2010

(54) METHOD FOR DIAGNOSIS OF GLIOMA: DISTINGUISHING BETWEEN PROGRESSIVE AND DE NOVO TYPES

(75) Inventors: Kumaravel Somasundaram, Bangalore (IN); Alangar Sathyaranjandas Hegde, Bangalore (IN); Sridevi Hegde, Bangalore (IN); Paturu Kondaiah, Bangalore (IN); Manchanahalli Rangaswamy Satyanarayana Rao, Bangalore (IN)

(73) Assignee: Council of Scientific and Industrial Research, New Delhi (IN)

( * ) Notice: Subject to any disclaimer, the term of this patent is extended or adjusted under 35 U.S.C. 154(b) by 166 days.

(21) Appl. No.: 11/491,520

(22) Filed: Jul. 21, 2006

(65) Prior Publication Data

US 2007/0072216 A1 Mar. 29, 2007

(30) Foreign Application Priority Data

Jul. 26, 2005 (IN) .................... 1975/DEL/2005

(51) Int. Cl.
*C12Q 1/68* (2006.01)
(52) U.S. Cl. ........................................... 435/6
(58) Field of Classification Search ............... None
See application file for complete search history.

(56) References Cited

OTHER PUBLICATIONS

Kanamori et al. J. Neurosurg 2007 vol. 106 p. 417.*
Phillips et al. 2006 Cancer Cell vol. 9 p. 157.*
Altschul, S., et al., "Gapped BLAST And PSI-BLAST: A New Generation Of Protein Database Search Programs," *Nucleic Acids Research*, 25(17):3389-3402 (1997).
Bee, S., et al, "The bHLH Gene *Hes6*, An Inhibitor Of *Hes1*, Promotes Neuronal Differentiation,"*Development*, 127:2933-2943 (2000).
Casarosa, S., et al., "*Mash1* Regulates Neurogenesis in the Ventral Telencephalon," *Development*, 126:526-534 1999.
Fathallah-Shaykh, H., et al, "Mathematical Modeling Of Noise and Discovery Of Genetic Expression Classes in Gliomas," *Oncogene*, 21:7164-7174 (2002).
Frederick, L., et al. "Diversity And Frequency Of Epidermal Growth Factor Receptor Mutations in Human Glioblastomas," *Cancer Research*, 60:1383-1387 (2000).
Godard, S., et al., "Classification Of Human Astrocytic Gliomas On The Basis Of Gene Expression: A Correlated Group Of Genes With Angiogenic Activity Emerges As A Strong Predictor Of Subtypes," *Cancer Res.*, 63:6613-6625 (2003).
Heitzler, P., et al., "Genes Of The *Enhancer Of Split* And *Achaete-Scute* Complexes Are Required For A Regulatory Loop Between *Notch And Delta* During Lateral Signalling in *Drosophila*," *Development*, 122:161-171 (1996).
Hermanson, M., et al., "Platelet-Derived Growth Factor And Its Receptors in Human Glioma Tissue: Expression Of Messenger RNA And Protein Suggests The Presence Of Autocrine And Paracrine Loops," *Cancer Res.*, 52:3213-3219 (1992).
Hermanson, M., et al., "Association Of Loss Of Heterozygosity On Chromosome 17p With High Platelet-Derived Growth Factor Alpha Receptor Expression in Human Malignant Gliomas," *Cancer Res.*, 56:164-171 (Jan. 1996).
Hill, J, et al., "Molecular Genetics Of Brain Tumors," *Arch Neurol.*, 56:439-441 (Apr. 1999).
Landis, S., et al., "Cancer Statistics, 1999," *CA-A Cancer J. Clin.*, 49(1):8-31 (1999).
Maher, E., et al., "Malignant Glioma: Genetics And Biology Of A Grave Matter," *Genes Dev.*, 15:1311-1333 (2001).
Muller, P., et al., "The Anti-Estrogenic Effect Of All-*Trans*-Retinoic Acid On The Breast Cancer Cell Line MCF-7 Is Dependent On HES-1 Expression," *J. Biol. Chem.*, 277(32):28376-28379 (Aug. 2002).
Olopade, O., et al., "Molecular Analysis Of Deletions Of The Short Arm Of Chromosome 9 in Human Gliomas," *Cancer Res.*, 52;2523-2529 (May 1992).
Rickman, D., et al., "Distinctive Molecular Profiles Of High-Grade And Low-Grade Gliomas Based On Oligonucleotide Microarray Analysis," *Cancer Res.*, 61:6885-6891 (Sep. 2001).
Sallinen S., et al., "Identification Of Differentially Expressed Genes in Human Gliomas by DNA Microarray And Tissue Chip Techniques," *Cancer Res.*, 60:6617-6622 (Dec. 2000).
Schmidt D. and Muller, S., "Members Of The PIAS Family Act As SUMO Ligases for c-Jun And p53 And Repress p53 Activity," *Proc Natl Acad Sci USA*, 99(5):2872-2877 (Mar. 2002).
Tanwar, M., et al., "Gene Expression Microarray Analysis Reveals YKL-40 To Be A Potential Serum Marker For Malignant Character in Human Glioma," *Cancer Res.*, 62:4364-4368 (Aug. 2002).
Watanabe, K., et al,, "Incidence And Timing Of p53 Mutations During Astrocytoma Progression in Patients With Multiple Biopsies," *Clin. Cancer Res.*, 3:523-530 (Apr. 1997).
Zhang, J. and Madden, TL., "Power BLAST: A New Network BLAST Application For Interactive Or Automated Sequence Analysis And Annotation," *Genome Res.*, 7:649-656 (1997).
Altschul, S., et al., "Basic local alignment search tool," *J. Mol. Biol.*, 215(3):403-410 (1990).
Apelqvist, A., et al., "Notch signaling controls pancreatic cell differentiation," *Nature*, 400(6747):877-881 (1999).
Artavanis-Tsakonas, S., et al., "Notch signaling," *Science*, 268(5208):225-232 (1995).
Artavanis-Tsakonas, S., et al., "Notch signaling: cell fate control and signal integration in development," *Science*, 284(5415):770-776 (1999).

(Continued)

*Primary Examiner*—Sarae Bausch
*Assistant Examiner*—Katherine Salmon
(74) *Attorney, Agent, or Firm*—Brinks Hofer Gilson & Lione

(57) ABSTRACT

The present invention relates to a method for identifying the type of glioblastoma multiforme in mammals, preferably human subjects. More particularly, it relates to a kit for characterizing progressive glioma in mammals, preferably human subjects. More particularly, it relates to a kit for distinguishing primary and secondary glioblastoma multiforme (GBM) in mammals, preferably human subjects.

6 Claims, 3 Drawing Sheets

OTHER PUBLICATIONS

Bonni, A., et al., "Regulation of gliogenesis in the central nervous system by the JAK-STAT signaling pathway," *Science*, 278(5337):477-483 (1997).

Brock, C. and Bower, M., "Current perspectives in gliomas," *Med Oncol.*, 14(2):103-120 (1997).

Campomenosi, P., et al., "Study on aneuploidy and p53 mutations in astrocytomas," *Cancer Genet Cytogenet*, 88(2):95-102 (1996).

Daumas-Duport, C., "Histoprognosis of gliomas," *Adv. Tech. Stand Neurosurg.*, 21:43-76 (1994).

Davis, F., et al., "Survival rates in patients with primary malignant brain tumors stratified by patient age and tumor histological type: an analysis based on Surveillance, Epidemiology, and End Results (SEER) data, 1973-1991," *Neurosurg.*, 88(1):1-10 (1998).

DeAngelis, L., "Primary central nervous system lymphomas," *Curr. Treat. Options Oncol*, 2(4):309-318 (2001).

Di, X., et al., "Poliferative potentials of glioma cells and vascular components determined with monoclonal antibody MIB-1," *J. Exp. Clin. Cancer Res.*, 16(2):153-157 (1997).

Ellisen, L., et al., "*TAN-1*, the human homolog of the *Drosphila notch* gene, is broken by chromosomal translocations in T lymphoblastic neoplasms," *Cell*, 66(4):649-661 (1991).

Ghysen, A., et al., "Cell interactions and gene interactions in peripheral neurogenesis," *Genes Dev.*, 7(5):723-733 (1993).

Gilbert, J., et al., "Transscleral permeability and intraocular concentrations of cisplatin from a collagen matrix," *J. Control Release*, 89(3):409-417 (2003).

Golub, T., at al., "Molecular classification of cancer: class discovery and class prediction by gene expression monitoring," *Science*, 286(5439):531-537 (1999).

Haltiwanger, R., Stanley, P,, "Modulation of receptor signaling by glycosylation: fringe is an O-fucose-beta1,3-N-acetylglucosaminyltransferase," *Biochim et Biophys Acta.*, 1573(3):328-335 (2002).

Johe, K., et al., "Single factors direct the differentiation of stem cells from the fetal and adult central nervous system," *Genes Dev.*, 10(214):3129-3140 (1996).

Kleihues, P., Ohgaki, H., "Phenotype vs genotype in the evolution of astrocytic brain tumors," *Toxicol Pathol.*, 28(1).164-170 (2000).

Kleihues, P., et al., "The WHO classification of tumors of the nervous system," *J. Neuropathol Exp Neurol*, 61(3):215-225 (2002).

Li, A.,"Comparative study of methods of active effects on human brain to reveal abilities of low level perception," *Biofizika*, 42(3):711-717 (1997).

Liau L., et al., "Identification of a human glioma-associated growth factor gene, *granulin*, using differential immuno-absorption," *Cancer Res.*, 60(5):1353-1360 (2000).

Ljubimova, J., et al,, "Overexpression of α4 chain-containing laminins in human glial tumors identified by gene microarray analysis," *Cancer Res.*, 61(14):5601-5610 (2001).

Ljubimova, J., et al., "Gene expression abnormalities in human glial tumors identified by gene array," *Int J. Oncol.*, 18(2):287-295 (2001).

Louis, D., Gusella, J., "A tiger behind many doors: multiple genetic pathways to malignant glioma," *Trends Genet*, 11(10):412-415 (1995).

Madden, T., et al., "Applications of network BLAST server," *Methods Enzymol.*, 266:131-141 (1996).

Morrison, S., et al., "Transient Notch activation initiates an irreversible switch from neurogenesis to gliogenesis by neural crest stem cells," *Cell*, 101(5):499-510 (2002).

Nagane, M., et al. "Application of antisense ribonucleic acid complementary to $O^6$-methylguanine-deoxyribonucleic acid methyltransferase messenger ribonucleic acid for therapy of malignant gliomas," *Neurosurgery*, 41(2):434-440 (1997).

Nagane, M., et al., "Advances in the molecular genetics of gliomas," *Curr. Opin. Oncol.*, 3(3):215-222 (1997).

Novitch, B., et al., "Coordinate regulation of motor neuron subtype identity and pan-neuronal properties by the bHLH repressor Olig2," *Neuron*, 31(5):773-789 (2001).

Nicolas, M., et al., "Notch1 functions as a tumor suppressor in mouse skin," *Nat. Genet.*, 33(3):416-421 (2003).

Nieto, M., et al., "Neural bHLH genes control the neuronal versus glial fate decision in cortical progenitors," *Neuron*, 29(2):401-413 (2001).

Nutt, C., et al., "Gene expression-based classification of malignant gliomas correlates better with survival then histological classification," *Cancer Res.*, 63(7):1062-1607 (2003).

Phatak, P., et al., "Alterations in tumour suppressor gene p53 in human gliomas form Indian patients," *J. Biosci.*, 27(7):673-8 (2002).

Post, L., et al., "Notch/Delta expression in the developing mouse lung," *Mech. Dev.*, 98(1-2):95-98 (2000).

Qian, Y., et al., "Lead targets GRP78, a molecular chaperone, in C6 rat glioma cells," *Toxicol. Appl. Pharmacol.*, 163(3):260-266 (2000).

Rangarajan, A., et al., "Activated Notch1 signaling cooperates with Papillomavirus oncogenes in transformation and generates resistance to apoptosis on matrix withdrawal through PKB/Akt," *Virology*, 286(1):23-30 (2001).

Sakamoto, K., et al., "Intracellular cell-autonomous association of Notch and its ligands: a novel mechanism of Notch signal modification," *Dev Biol.*, 241(2):313-326 (2002).

Schiffer, D., et al., "Cell proliferation and invasion in malignant gliomas," *Anticancer Res.*, 17(1A):61-70 (1997).

Ström, A., et al., "The *Hairy* and *Enhancer of Spilt* homologue-1 (HES-1) mediates the proliferative effect of 17β-estradiol on breast cancer cell lines," *Oncogene*, 19(51):5951-5953 (2000).

Sun, X., et al., "Expression of P53 during lens epithelial cell apoptosis induced by ultraviolet," *J. Tongji Med. Univ.*, 21(3):263-264 (2001).

Swearingen, M., et al., "Detection of differentially expressed HES-6 gene in metastatic colon carcinoma by combination of suppression subtractive hybridization and cDNA library array," *Cancer Lett.*, 198(2):229-239 (2003).

Tanigaki, K., et al., "Notch1 and Notch3 instructively restrict bFGF-responsive multipotent neural progenitor cells to an astroglial fate," *Neuron*, 29(1):45-55 (2001).

Tews, D., Nissen, A., "Expression of adhesion factors and degrading proteins in primary and secondary glioblastomas and their precursor tumors," *Invasion Metastasis*, 18(5-6):271-284 (1998-1999).

Watson, G., at al., "Multidisciplinary management of pediatric low-grade gliomas," *Semin Radiat Oncol.*, 11(2):152-162 (2001).

Weinmaster, G., "The ins and outs of notch signaling," *Mol. Cell Neruosci.*, 9(2):91-102 (1997).

Westermark, B., et al. "Platelet-derived growth factor in human glioma," *Glia*, 15(3):257-263 (1995).

\* cited by examiner

SEQUENCE LISTING

```
<160> NUMBER OF SEQ ID NOS: 28

<210> SEQ ID NO 1
<211> LENGTH: 1471
<212> TYPE: DNA
```

<213> ORGANISM: Homo sapiens

<400> SEQUENCE: 1

```
atcacacagg atccggagct ggtgctgata acagcggaat ccccgtcta cctctctcct       60
tggtcctgga acagcgctac tgatcaccaa gtagccacaa aatataataa accctcagca      120
cttgctcagt agttttgtga aagtctcaag taaaagagac acaaacaaaa aattcttttt      180
cgtgaagaac tccaaaaata aaattctcta gagataaaaa aaaaaaaaa aggaaaatgc       240
cagctgatat aatggagaaa aattcctcgt ccccggtggc tgctacccca gccagtgtca      300
acacgacacc ggataaaacca agacagcat ctgagcacag aaagtcatca aagcctatta      360
tggagaaaag acgaagagca agaataaatg aaagtctgag ccagctgaaa acactgattt      420
tggatgctct gaagaaagat agctcgcggc attccaagct ggagaaggcg acattctgg       480
aaatgacagt gaagcacctc cggaacctgc agcgggcgca gatgacggct gcgctgagca      540
cagacccaag tgtgctgggg aagtaccgag ccggcttcag cgagtgcatg aacgaggtga      600
cccgcttcct gtccacgtgc gagggcgtta ataccgaggt gcgcactcgg ctgctcggcc      660
acctggccaa ctgcatgacc cagatcaatg ccatgaccta ccccgggcag ccgcacccccg     720
ccttgcaggc gccgccaccg ccccaccgg acccggcgg ccccagcac gcgccgttcg         780
cgccgccgcc gccactcgtg cccatccccg ggggcgcggc gcccctccc ggcggcgccc       840
cctgcaagct gggcagccag gctggagagg cggctaaggt gtttggaggc ttccaggtgg      900
taccggctcc cgatggccag tttgctttcc tcattcccaa cggggccttc gcgcacagcg      960
gccctgtcat ccccgtctac accagcaaca gcggcacctc cgtgggcccc aacgcagtgt     1020
caccttccag cggccctcg cttacggcgg actccatgtg gaggccgtgg cggaactgag      1080
ggggctcagg ccaccctcc tctaaactc cccaacccac ctctcttccc tccggactct       1140
aaacaggaac ttgaatactg ggagagaaga ggacttttttt gattaagtgg ttactttgtg     1200
tttttttaat ttctaagaag ttacttttg tagagagagc tgtattaagt gactgaccat       1260
gcactatatt tgtatatatt ttatatgttc atattggatt gcgcctttgt attataaaag     1320
ctcagatgac atttcgtttt ttacacgaga tttcttttt atgtgatgcc aaagatgttt      1380
gaaaatgctc ttaaaatatc ttcctttggg gaagtttatt tgagaaaata taataaaga      1440
aaaaagtaaa ggcaaaaaaaa aaaaaaaaaa a                                    1471
```

<210> SEQ ID NO 2
<211> LENGTH: 2660
<212> TYPE: DNA
<213> ORGANISM: Homo sapiens

<400> SEQUENCE: 2

```
cattggctga aagttactgt gggaaagaaa gtttgggaag tttcacacga gccgttcgcg       60
tgcagtccca gatatatata gaggccgcca gggcctaggg atcacacagg atccggagct      120
ggtgctgata acagcggaat ccccgtcta cctctctcct tggtcctgga acagcgctac      180
tgatcaccaa gtagccacaa aatataataa accctcagca cttgctcagt agttttgtga     240
aagtctcaag taaaagagac acaaacaaaa aattcttttt cgtgaagaac tccaaaaata     300
aaattctcta gagataaaaa aaaaaaaaa aggaaaatgc cagctgatat atggagaaaa       360
attcctcgtc cccggtggct gctacccccag ccagtgtcaa cacgacaccg gataaaccaa    420
agacagcatc tgagcacaga aaggtaaggg cggtacctgt atctctttgc agccctcaa      480
aattaagtag gggttggggg gcttctttct gtcttgaaac ccgggatgg cagattccat      540
```

```
gggaacacag aactcttttt tttatttgca gtcatcaaag cctattatgg agaaaagacg    600
aagagcaaga ataaatgaaa gtctgagcca gctgaaaaca ctgattttgg atgctctgaa    660
gaaagatgta agtggggaaa tgctgctcgc tcttttaatt aaaaaacaaa cactttctca    720
gctactaaga gtgaaacccc ccgccctgcg gggtctggca ctcgctggta ctgcgttctc    780
ccaggcggga gggcccggcc ttattcgctg gggtccagag ataatgcttg cgctccgtgg    840
ccgggaggag ggacccccag cactctgaag cagctgacac ggggctcact ttcctttctt    900
gcctactcta tgcagagctc gcggcattcc aagctggaga aggcggacat tctggaaatg    960
acagtgaagc acctccggaa cctgcagcgg gcgcagatga cgggtgaggg cggctcgccg   1020
cgtccccctg tgcgggcgtc ccgctcgcct cgcggtgatt tcttccagac ttccgcccgt   1080
ggttgtgaga ggcattcaga cattttactg ccttggctca ctcttgcgtt cccacggtct   1140
ggggcttatt tatagccaca actccaagtt gttactgttc cggaagggga gggaaagagg   1200
ttgcagccgc gagggtggcg ggcgccgggt agggggcgaaa ggacttagga ctgtggcggt   1260
ttggaactgc gtggagcctg ggggtcactg gtttagcact ccttcccgtt gcagaagggg   1320
aaatgaggct tggatgatgg attgggaggc attgtccaag gtcacatcgc gcgcggggt   1380
gggggtgaca gatctgggc tgagataggt ttaaatgcag ctacagggaa tcggaaggga   1440
gtggctcggc ttttggcagc aacgctagtg tggagaggtg gctggttttt tctaaaccca   1500
tctcaccctc cctgccggag gcagtttcac gggcgcatgg tcaggaggc gcgccacagg   1560
gacctcccag ggcggaggca gtggccacgg ggccagggcc gttcggtgac ccgtctgtct   1620
ctttctggcc cgcagctgcg ctgagcacag acccaagtgt gctggggaag taccgagccg   1680
gcttcagcga gtgcatgaac gaggtgaccc gcttcctgtc cacgtgcgag ggcgttaata   1740
ccgaggtgcg cactcggctg ctcggccacc tggccaactg catgacccag atcaatgcca   1800
tgacctaccc cgggcagccg caccccgcct tgcaggcgcc gccaccgccc caccgggac   1860
ccggcggccc ccagcacgcg ccgttcgcgc cgccgccgcc actcgtgccc atccccgggg   1920
gcgcggcgcc ccctcccggc ggcgccccct gcaagctggg cagccaggct ggagaggcgg   1980
ctaaggtgtt tggaggcttc caggtggtac cggctcccga tggccagttt gctttcctca   2040
ttcccaacgg ggccttcgcg cacagcggcc ctgtcatccc cgtctacacc agcaacagcg   2100
gcacctccgt gggccccaac gcagtgtcac cttccagcgg cccctcgctt acggcggact   2160
ccatgtggag gccgtggcgg aactgagggg gctcaggcca cccctcctcc taaactcccc   2220
aacccacctc tcttccctcc ggactctaaa caggaacttg aatactggga gagaagagga   2280
cttttttgat taagtggtta ctttgtgttt tttaatttc taagaagtta cttttttgtag   2340
agagagctgt attaagtgac tgaccatgca ctatatttgt atatattta tatgttcata   2400
ttggattgcg cctttgtatt ataaaagctc agatgacatt tcgttttta cacgagattt   2460
cttttttatg tgatgccaaa gatgtttgaa aatgctctta aaatatcttc ctttggggaa   2520
gtttatttga gaaaatataa taaaagaaaa aagtaaaggc ttttatgtct tcgaactgat   2580
tcttccagaa tatgtaaaaa ggcttttggt ggaatttgaa ttacatgtaa ttggtaattc   2640
aggaattgac tcttttgtta                                              2660
```

<210> SEQ ID NO 3
<211> LENGTH: 2482
<212> TYPE: DNA
<213> ORGANISM: Homo sapiens

<400> SEQUENCE: 3

```
cttctggcca gggaacgtgg aaggcgcacc gacagggatc cggccaggga gggcgagtga      60
aagaaggaaa tcagaaagga agggagttaa caaaataata aaaacagcct gagccacggc     120
tggagagacc gagacccggc gcaagagagc gcagccttag taggagagga acgcgagacg     180
cggcagagcg cgttcagcac tgacttttgc tgctgcttct gctttttttt ttcttagaaa     240
caagaaggcg ccagcggcag cctcacacgc gagcgccacg cgaggctccc gaagccaacc     300
cgcgaaggga ggaggggagg gaggaggagg cggcgtgcag ggaggagaaa aagcattttc     360
acttttttg ctcccactct aagaagtctc ccggggattt tgtatatatt ttttaacttc     420
cgtcagggct cccgcttcat atttcctttt ctttccctct ctgttcctgc acccaagttc     480
tctctgtgtc cccctcgcgg gccccgcacc tcgcgtcccg gatcgctctg attccgcgac     540
tccttggccg ccgctgcgca tggaaagctc tgccaagatg gagagcggcg gcgccggcca     600
gcagccccag ccgcagcccc agcagccctt cctgccgccc gcagcctgtt ctttgccac     660
ggccgcagcc gcggcggccg cagccgccgc agcggcagcg cagagcgcgc agcagcagca     720
gcagcagcag cagcagcagc agcaggcgcc gcagctgaga ccggcggccg acggccagcc     780
ctcaggggc ggtcacaagt cagcgcccaa gcaagtcaag cgacagcgct cgtcttcgcc     840
cgaactgatg cgctgcaaac gccggctcaa cttcagcggc tttggctaca gcctgccgca     900
gcagcagccg gccgccgtgg cgcgccgcaa cgagcgcgag cgcaaccgcg tcaagttggt     960
caacctgggc tttgccaccc ttcgggagca cgtccccaac ggcgcggcca acaagaagat    1020
gagtaaggtg gagacactgc gctcggcggt cgagtacatc cgcgcgctgc agcagctgct    1080
ggacgagcat gacgcggtga gcgccgcctt ccaggcaggc gtcctgtcgc ccaccatctc    1140
ccccaactac tccaacgact tgaactccat ggccggctcg ccggtctcat cctactcgtc    1200
ggacgagggc tcttacgacc cgctcagccc cgaggagcag gagcttctcg acttcaccaa    1260
ctggttctga ggggctcggc ctggtcaggc cctggtgcga atggactttg gaagcagggt    1320
gatcgcacaa cctgcatctt tagtgctttc ttgtcagtgg cgttgggagg gggagaaaag    1380
gaaaagaaaa aaaaagaag aagaagaaga aagagaagaa agaaaaaaac gaaaacagtc    1440
aaccaacccc atcgccaact aagcgaggca tgcctgagag acatggcttt cagaaaacgg    1500
gaagcgctca gaacagtatc tttgcactcc aatcattcac ggagatatga agagcaactg    1560
ggacctgagt caatgcgcaa aatgcagctt gtgtgcaaaa gcagtgggct cctggcagaa    1620
gggagcagca cacgcgttat agtaactccc atcacctcta acacgcacag ctgaaagttc    1680
ttgctcgggt cccttcacct ccccgcccctt tcttaaagtg cagttcttag ccctctagaa    1740
acgagttggt gtctttcgtc tcagtagccc caccccaat aagctgtaga cattggttta    1800
cagtgaaact atgctattct cagccctttg aaactctgct tctcctccag ggcccgattc    1860
ccaaacccca tggcttccct cacactgtct tttctaccat tttcattata gaatgcttcc    1920
aatcttttgt gaattttta ttataaaaaa tctatttgta tctatcctaa ccagttcggg    1980
gatatattaa gatatttttg tacataagag agaaagagag agaaaaattt atagaagttt    2040
tgtacaaatg gtttaaaatg tgtatatctt gatactttaa catgtaatgc tattacctct    2100
gcatatttta gatgtgtagt tcaccttaca actgcaattt tccctatgtg gttttgtaaa    2160
gaactctcct cataggtgag atcaagaggc caccagttgt acttcagcac caatgtgtct    2220
tactttatag aaatgttgtt aatgtattaa tgatgttatt aaatactgtt caagaagaac    2280
aaagtttatg cagctactgt ccaaactcaa agtggcagcc agttggtttt gataggttgc    2340
```

```
cttttggaga tttctattac tgccttttt  ttcttactgt tttattacaa acttacaaaa      2400
atatgtataa ccctgtttta tacaaactag tttcgtaata aaacttttc  cttttttaa      2460 aatgaaaaaa aaaaaaaaaa aa                                               2482

<210> SEQ ID NO 4
<211> LENGTH: 3028
<212> TYPE: DNA
<213> ORGANISM: Homo sapiens

<400> SEQUENCE: 4
agcagcgggg agtgggggc  gaggcgggc  cagggctgcg cgtggggctg ggtgtcccat        60
tgaaaaggcg gacgcactcc ggcagcccag cactctctca cttctggcca gggaacgtgg      120
aaggcgcacc gacagggatc cggccaggga gggcgagtga agaaggaaa  tcagaaagga      180 agggagttaa caaaataata aaaacagcct gagccacggc tggagagacc gagacccggc      240
gcaagagagc gcagccttag taggagagga acgcgagacg cggcagagcg cgttcagcac      300
tgacttttgc tgctgcttct gcttttttt  ttcttagaaa caagaaggcg ccagcggcag      360
cctcacacgc gagcgccacg cgaggctccc gaagccaacc cgcgaaggga ggaggggagg      420
gaggaggagg cggcgtgcag ggaggagaaa aagcattttc acttttttg  ctcccactct      480 aagaagtctc ccggggattt tgtatatatt ttttaacttc cgtcagggct cccgcttcat      540 atttccttt  ctttccctct ctgttcctgc acccaagttc tctctgtgtc cccctcgcgg      600
gccccgcacc tcgcgtcccg gatcgctctg attccgcgac tccttggccg ccgctgcgca      660
tggaaagctc tgccaagatg gagagcggcg gcgccggcca gcagcccag  ccgcagcccc      720 agcagccctt cctgccgccc gcagcctgtt tctttgccac ggccgcagcc gcggcggccg      780
cagccgccgc agcggcagcg cagagcgcgc agcagcagca gcagcagcag cagcagcagc      840
agcaggcgcc gcagctgaga ccggcggccg acggccagcc ctcaggggcc ggtcacaagt      900
cagcgcccaa gcaagtcaag cgacagcgct cgtcttcgcc cgaactgatg cgctgcaaac      960
gccggctcaa cttcagcggc tttggctaca gcctgccgca gcagcagccg ccgccgtgg     1020 cgcgccgcaa cgagcgcgag cgcaaccgcg tcaagttggt caacctgggc tttgccaccc     1080
ttcgggagca cgtccccaac ggcgcggcca acaagaagat gagtaaggtg gagacactgc     1140
gctcggcggt cgagtacatc cgcgcgctgc agcagctgct ggacgagcat gacgcggtga     1200
gcgccgcctt ccaggcaggc gtcctgtcgc ccaccatctc ccccaactac tccaacgact     1260
tgaactccat ggccggctcg ccggtctcat cctactcgtc ggacgagggc tcttacgacc     1320
cgctcagccc cgaggagcag agcttctcg  acttcaccaa ctggttctga ggggctcggc     1380
ctggtcaggc cctggtgcga atggactttg gaagcaggta ggttgcattt tggggtgggc     1440 agggggtat  tcttgccttc gtcctcccctc tgagtgtctg tggaagtggg gatgtctcca     1500
aggagataag gggattttta tttaaagaat ttgtgaaagt tggtcgattt caagtcctag     1560
tttgttagtt tcagcactgg cctctgaaaa tggccttgcc caggtctcca aggagtgaag     1620
ggtagtagtg aggtgcagag atactggtga accgaatact gggacatgtt aaaagagatg     1680
tctacctgac agactctttc cccagacctc catctccctc taccactagc ctacacgttc     1740 aaattaaccct ctcctgttct tttccttatg ttataggggtg atcgcacaac ctgcatcttt    1800
agtgctttct tgtcagtggc gttgggaggg ggagaaaagg aaaagaaaaa aaaagaaga      1860 agaagaagaa aagagaagaa gaaaaaaacg aaaacagtca accaaccca  tcgccaacta     1920
```

| | |
|---|---|
| agcgaggcat gcctgagaga catggctttc agaaaacggg aagcgctcag aacagtatct | 1980 |
| ttgcactcca atcattcacg agatatgaa gagcaactgg gacctgagtc aatgcgcaaa | 2040 |
| atgcagcttg tgtgcaaaag cagtgggctc ctggcagaag ggagcagcac acgcgttata | 2100 |
| gtaactccca tcacctctaa cacgcacagc tgaaagttct tgctcgggtc ccttcacctc | 2160 |
| ctcgcccttt cttaaagtgc agttcttagc cctctagaaa cgagttggtg tctttcgtct | 2220 |
| cagtagcccc caccccaata agctgtagac attggtttac agtgaaacta tgctattctc | 2280 |
| agcccttga aactctgctt ctcctccagg gcccgattcc caaacccat ggcttccctc | 2340 |
| acactgtctt ttctaccatt ttcattatag aatgcttcca atcttttgtg aattttttat | 2400 |
| tataaaaaat ctatttgtat ctatcctaac cagttcgggg atatattaag atattttgt | 2460 |
| acataagaga gaaagagaga gaaaaattta tagaagtttt gtacaaatgg tttaaaatgt | 2520 |
| gtatatcttg atactttaac atgtaatgct attacctctg catattttag atgtgtagtt | 2580 |
| caccttacaa ctgcaatttt ccctatgtgg ttttgtaaag aactctcctc ataggtgaga | 2640 |
| tcaagaggcc accagttgta cttcagcacc aatgtgtctt actttataga aatgttgtta | 2700 |
| atgtattaat gatgttatta aatactgttc aagaagaaca aagtttatgc agctactgtc | 2760 |
| caaactcaaa gtggcagcca gttggttttg ataggttgcc ttttggagat ttctattact | 2820 |
| gccttttttt ttcttactgt tttattacaa acttacaaaa atatgtataa ccctgttta | 2880 |
| tacaaactag tttcgtaata aaactttttc cttttttaa aatgaaaata atcagctgac | 2940 |
| tctaagcttt ctttgactct gatgcccctg gtccagtttt atgaaaatgt caaagggaag | 3000 |
| aggtggatgg agaagaaaat gttgcaaa | 3028 |

<210> SEQ ID NO 5
<211> LENGTH: 1375
<212> TYPE: DNA
<213> ORGANISM: Homo sapiens

<400> SEQUENCE: 5

| | |
|---|---|
| ggagcgcgga cggctgggct gctgctgggc ggccgcgggg cagcggaggg cgccggcact | 60 |
| ccggtccccg ccgctccccg tccccgctgc tcctagcccc tgccgcgtcc ccggcggagc | 120 |
| gggcatggcg ccacccgcgg cgcctggccg ggaccgtgtg ggccgtgagg atgaggacgg | 180 |
| ctgggagacg cgaggggacc gcaaggcccg gaagcccctg gtggagaaga gcggcgcgc | 240 |
| gcggatcaac gagagcctgc aggagctgcg gctgctgctg gcgggcgccg aggtgcaggc | 300 |
| caagctggag aacgccgaag tgctggagct gacggtgcg cgggtccagg gtgtgctgcg | 360 |
| gggccgggcg cgcgagcgcg agcagctgca ggcggaagcg agcgagcgct tcgctgccgg | 420 |
| ctacatccag tgcatgcacg aggtgcacac gttcgtgtcc acgtgccagg ccatcgacgc | 480 |
| taccgtcgct gccgagctcc tgaaccatct gctcgagtcc atgccgctgc gtgagggcag | 540 |
| cagcttccag gatctgctgg gggacgccct ggcggggcca cctagagccc ctggacggag | 600 |
| tggctggcct gcgggggggcg ctccgggatc cccaatacccc agcccccgg gtcctgggga | 660 |
| cgacctgtgc tccgacctgg aggaggcccc tgaggctgaa ctgagtcagg ctcctgctga | 720 |
| ggggcccgac ttggtgcccg cagccctggg cagcctgacc acagcccaaa ttgcccggag | 780 |
| tgtctggagg ccttggtgac caatgccagc cagagtcctg cggggggtggg cccggccctc | 840 |
| cctggatctc ctccctcctc ccaggggttc agatgtggtg gggtagggcc ctggaagtct | 900 |
| cccaggtctt ccctccctcc tctgatggat ggcttgcagg gcagccctg gtaaccagcc | 960 |
| cagtcaggcc ccagccccgt ttcttaagaa acttttaggg accctgcagc tctggagtgg | 1020 |

```
gtggagggag ggagctacgg gcaggaggaa gaattttgta gagctgccag cgctctccca    1080
ggttcaccca cccagccttc accagccctg tgcgggctct gggggcagag gtggcaggaa    1140
tggtgctggg cactagtgtt ccaggcagcc ctgggctaaa caaaagcttg aacttgccac    1200
ttcagcgggg agatgagagg caggtgcact cagctgcact gcccagagct gtgatgctct    1260
gtacatcttg tttgtagcac acttgagttt gtgtattcca ttgacatcaa atgtgacaat    1320
tttactaaat aaagaatttt ggagttagtt acccttgaaa aaaaaaaaa aaaaa          1375

<210> SEQ ID NO 6
<211> LENGTH: 1963
<212> TYPE: DNA
<213> ORGANISM: Homo sapiens

<400> SEQUENCE: 6
tcgcggtcgg ccgccccggg cccgcgcggc aatcggcgc attgagatgc aaataagcgg      60
ctataaaagg ggcgggaccg cggcgggccg gaagccgcga ggagcgcgga cggctgggct    120
gctgctgggc ggccgcgggg cagcggaggg cgccggcact ccggtccccg ccgctccccg    180
tccccgctgc tcctagcccc tgccgcgtcc ccggcggagc gggcatggcg ccacccgcgg    240
cgcctggccg ggaccgtgtg ggccgtgagg atgaggacgg ctgggagacg cgagggggacc   300 gcaaggtgcg ggccggggcc atgggcgagc aagcgggcgg gaggccgtgc ggggctggga    360
ttcagtgccc cgctccccgc aggcccggaa gcccctggtg gagaagaagc ggcgcgcgcg    420
gatcaacgag agcctgcagg agctgcgcgt gctgctggcg ggcgccgagg tgcggcggcc    480
gggcaggcgc cgtggggctg cggggcgggc gggcgggtcc gggagcgcgc tgccggctca    540
ccgcccttcc cgcccgcgca ggtgcaggcc aagctggaga cgccgaagt gctggagctg     600 acggtgcggc gggtccaggg tgtgctgcgg ggccgggcgc gcggtgagtg gcggcggggc    660 gggcggggc gccggccgcg ggcgcctgta accctgcca gacggaggac ttccctcccg      720
gcgcccctgt cctgtcggcg gcgagggctc ccaccggagc agggtgcgcc ccgcgtctc     780 ctgggtgagc cgcgtccccg cgggccgggt gggctgggcc acgcagtcgc cgctcaccgc    840
gcgggacgcg gctctctccc tccaccctc gggcccagag cgcgagcagc tgcaggcgga    900
agcgagcgag cgcttcgctg ccggctacat ccagtgcatg cacgaggtgc acacgttcgt    960
gtccacgtgc caggccatcg acgctaccgt cgctgccgag ctcctgaacc atctgctcga   1020
gtccatgccg ctgcgtgagg gcagcagctt ccaggatctg ctgggggacg ccctggcggg   1080
gccacctaga gcccctggac ggagtggctg gcctgcgggg ggcgctccgg gatccccaat   1140
acccagcccc ccgggtcctg gggacgacct gtgctccgac ctggaggagg ccctgaggc    1200 tgaactgagt caggctcctg ctgaggggcc cgacttggtg cccgcagccc tgggcagcct   1260
gaccacagcc caaattgccc ggagtgtctg gaggccttgg tgaccaatgc cagccagagt   1320
cctgcggggg tgggccccggc cctccctgga tctcctccct cctcccaggg gttcagatgt   1380
ggtggggtag ggccctggaa gtctcccagg tcttccctcc ctcctctgat ggatggcttg   1440
cagggcagcc cctggtaacc agcccagtca ggccccagcc ccgtttctta agaaactttt   1500
agggaccctg cagctctgga gtgggtggag ggagggagct acgggcagga ggaagaattt   1560
tgtagagctg ccagcgctct cccaggttca cccacccagg cttcaccagc cctgtgcggg   1620
ctctgggggc agaggtggca gaaatggtgc tgggcactag tgttccaggc agccctgggc   1680
taaacaaaag cttgaacttg ccacttcagc ggggagatga gaggcaggtg cactgagctg   1740
```

-continued

| | | | |
|---|---|---|---|
| cactgcccag agctgtgatg ctctgtacat cttgtttgta gcacacttga gtttgtgtat | | | 1800 |
| tccattgaca tcaaatgtga caattttact aaataaagaa ttttggagtt agttacccct | | | 1860 |
| gaagtattgt tgagtgatgt gtcattactg tgtcaagata tgtaaatgct aaactaagca | | | 1920 |
| catttcccct gcatctgagg ctggtgaatg tcctttaaaa cct | | | 1963 |

```
<210> SEQ ID NO 7
<211> LENGTH: 3158
<212> TYPE: DNA
<213> ORGANISM: Homo sapiens

<400> SEQUENCE: 7
```

| | | | |
|---|---|---|---|
| aaaccggaac ggggcccaac ttctggggcc tggagaaggg aaacgaagtc cccccggtt | | | 60 |
| tcccgaggtt gcctttcctc gggcatcctt ggtttcggcg ggacttcgca gggcggatat | | | 120 |
| aaagaacggc gcctttggga agaggcggag accggcttta agaaagaag tcttggtcct | | | 180 |
| gcggcttggg cgaggcaagg gcgaggcaag ggcgctttct gccgacgctc cccgtggccc | | | 240 |
| tacgatcccc cgcgcgtccg ccgctgttct aaggagagaa gtgggggccc cccaggctcg | | | 300 |
| cgcgtggagc gaagcagcat gggcagtcgg tgcgcgctgg ccctggcggt gctctcggcc | | | 360 |
| ttgctgtgtc aggtctggag ctctggggtg ttcgaactga agctgcagga gttcgtcaac | | | 420 |
| aagaagggc tgctggggaa ccgcaactgc tgccgcgggg gcgcggggcc accgccgtgc | | | 480 |
| gcctgccgga ccttcttccg cgtgtgcctc aagcactacc aggccagcgt gtccccgag | | | 540 |
| ccgcccctgca cctacggcag cgccgtcacc ccgtgctgg gcgtcgactc cttcagtctg | | | 600 |
| cccgacggcg ggggcgccga ctccgcgttc agcaacccca tccgcttccc cttcggcttc | | | 660 |
| acctggccgg gcaccttctc tctgattatt gaagctctcc acacagattc tcctgatgac | | | 720 |
| ctcgcaacag aaaacccaga aagactcatc agccgcctgg ccacccagag gcacctgacg | | | 780 |
| gtgggcgagg agtggtccca ggacctgcac agcagcggcc gcacggacct caagtactcc | | | 840 |
| taccgcttcg tgtgtgacga acactactac ggagagggct gctccgtttt ctgccgtccc | | | 900 |
| cgggacgatg ccttcggcca cttcacctgt ggggagcgtg gggagaaagt gtgcaaccct | | | 960 |
| ggctggaaag ggccctactg cacagagccg atctgcctgc ctggatgtga tgagcagcat | | | 1020 |
| ggattttgtg acaaaccagg ggaatgcaag tgcagagtgg gctggcaggg ccggtactgt | | | 1080 |
| gacgagtgta tccgctatcc aggctgtctc catggcacct gccagcagcc ctggcagtgc | | | 1140 |
| aactgccagg aaggctgggg gggcttttc tgcaaccagg acctgaacta ctgcacacac | | | 1200 |
| cataagccct gcaagaatgg agccacctgc accaacacgg gccaggggag ctacacttgc | | | 1260 |
| tcttgccggc ctgggtacac aggtgccacc tgcgagctgg ggattgacga gtgtgacccc | | | 1320 |
| agcccttgta gaacggagg gagctgcacg gatctcgaga cagctactc ctgtacctgc | | | 1380 |
| ccacccggct tctacggcaa aatctgtgaa ttgagtgcca tgacctgtgc ggacggccct | | | 1440 |
| tgctttaacg ggggtcggtg ctcagacagc cccgatggag ggtacagctg ccgctgcccc | | | 1500 |
| gtgggctact ccggcttcaa ctgtgagaag aaaattgact actgcagctc ttcaccctgt | | | 1560 |
| tctaatggtg ccaagtgtgt ggacctcggt gatgcctacc tgtgccgctg ccaggccggc | | | 1620 |
| ttctcgggga ggcactgtga cgacaacgtg gacgactgcg cctcctcccc gtgcgccaac | | | 1680 |
| gggggcacct gccgggatgg cgtgaacgac ttctcctgca cctgcccgcc tggctacacg | | | 1740 |
| ggcaggaact gcagtgcccc cgtcagcagg tgcgagcacg cccctgccaa caatggggcc | | | 1800 |
| acctgccacc agagggggcca cggctatgtg tgcgaatgtg cccgaagcta cggggggtccc | | | 1860 |
| aactgccagt tcctgctccc cgagctgccc ccgggcccag cggtggtgga cctcactgag | | | 1920 |

-continued

```
aagctagagg gccagggcgg gccattcccc tgggtggccg tgtgcgccgg ggtcatcctt       1980
gtcctcatgc tgctgctggg ctgtgccgct gtggtggtct gcgtccggct gaggctgcag       2040
aagcaccggc ccccagccga cccctgccgg ggggagacgg agaccatgaa caacctggcc       2100
aactgccagc gtgagaagga catctcagtc agcatcatcg gggccacgca gatcaagaac       2160
accaacaaga aggcggactt ccacggggac acagcgccg acaagaatgg cttcaaggcc        2220
cgctacccag cggtggacta taacctcgtg caggacctca agggtgacga caccgccgtc       2280
agggacgcgc acagcaagcg tgacaccaag tgccagcccc agggctcctc aggggaggag       2340
aaggggaccc cgaccacact caggggtgga gaagcatctg aaagaaaaag gccggactcg       2400
ggctgttcaa cttcaaaaga caccaagtac cagtcggtgt acgtcatatc cgaggagaag       2460
gatgagtgcg tcatagcaac tgaggtgtaa atggaagtg agatggcaag actcccgttt        2520
ctcttaaaat aagtaaaatt ccaaggatat atgccccaac gaatgctgct gaagaggagg       2580
gaggcctcgt ggactgctgc tgagaaaccg agttcagacc gagcaggttc tcctcctgag       2640
gtcctcgacg cctgccgaca gcctgtcgcg gccccggccgc ctgcggcact gccttccgtg      2700
acgtcgccgt tgcactatgg acagttgctc ttaagagaat atatatttaa atgggtgaac       2760
tgaattacgc ctaagaagca tgcactgcct gagtgtatat tttggattct tatgagccag       2820
tcttttcttg aattagaaac acaaacactg ccttattgt cctttttgat acgaagatgt        2880
gcttttctta gatggaaaag atgtgtgtta ttttttggat ttgtaaaaat attttttcatg      2940
atatctgtaa agcttgagta ttttgtgatg ttcgtttttt ataatttaaa ttttggtaaa       3000
tatgtacaaa ggcacttcgg gtctatgtga ctatatttt ttgtatataa atgtatttat        3060
ggaatattgt gccaatgtta tttgagtttt ttactgtttt gttaatgaag aaattccttt       3120
ttaaaatatt tttccaaaat aaattttatg aggaattc                               3158
```

<210> SEQ ID NO 8
<211> LENGTH: 8380
<212> TYPE: DNA
<213> ORGANISM: Homo sapiens

<400> SEQUENCE: 8

```
tgcgaagaag ctcaagacaa aaccaggaag ccggcgaccc tcacctcctc gggggctggg         60
aggaaggagg aaaacgaaag tcgccgccgc cgcgctgtcc cccgagagct gccttttcctc       120
gggcatccct ggggctgccg cgggacctcg cagggcggat ataaagaacc gcggccttgg       180
gaagaggcgg agaccggctt ttaaagaaag aagtcctggg tcctgcggtc tggggcgagg       240
caagggcgct tttctgccca cgctccccgt ggcccatcga tccccccgcgc gtccgccgct       300
gttctaagga gagaagtggg ggccccccag gctcgcgcgt ggagcgaagc agcatgggca       360
gtcggtgcgc gctggccctg gcggtgctct cggccttgct gtgtcaggta ggcgggcagg       420
tgggggcgcc gcggccccgc ggggtctcac gggtagccgg ggcgcggggc aggagcgcgc       480
ggggaggggc ggacagcggc acgggccgcg ccagccacgg cccggaagat gaatcccggg       540
ggcgacgacc ccagcgccgg ccgtgcagcg agcgcgctcg gcccctgagc ccttccaggc       600
tctccgcaca cccccaccc aggcctcacg cccctagct cgggcgggac ccgcgtcctc         660
acgcccccgc cctccccgt gcaggtctgg agctctgggg tgttcgaact gaagctgcag       720
gagttcgtca acaagaaggg gctgctgggg aaccgcaact gctgccgcgg gggcgcgggg      780
ccaccgccgt gcgcctgccg gaccttcttc cgcgtgtgcc tcaagcacta ccaggccagc       840
```

| | |
|---|---|
| gtgtccccg agccgccctg cacctacggc agcgccgtca ccccgtgct gggcgtcgac | 900 |
| tccttcagtc tgcccgacgg cggggcgcc gactccgcgt tcagcaaccc catccgcttc | 960 |
| cccttcggct tcacctggcc ggtgagtgcc gcacctgcgc gcgccgggcc ggccctgaag | 1020 |
| ctgggcgggc tgcaggacgc gctgggatcc cgccttgggc gctcggtggc gggacctcgg | 1080 |
| ggaccccgcg aggcgcaggt gggcgctgcg atctgcctag cggcggcccc aggactccag | 1140 |
| cccagcagcg cggacacctc gcccgggc cccgcgcct gcaggagggg accgcgctgg | 1200 |
| ggcgaggagg agaggccgag cgcgcccggg agatttccgt atccggcctc tgtgccaggt | 1260 |
| ctccagtcag aggcgcccct tcacgtggga aggttctggt ttcccgactc ctagacgcgt | 1320 |
| tggtggcgcg attaccgcg cagcgcgacc gctaccaccc ggagcgtgcc catcccccaa | 1380 |
| gaaaaatgac aagggccctc gggcctcttc cacccatcc tgcctgcatt ctctctctct | 1440 |
| ctctaattaa aaaacaacg taatatcctg tagtacaggc tgaaaaaaca cgtcaggaaa | 1500 |
| ccactcttta aaaagttctt ccatttcctt agggaaggtg agagcaggca ggaggtgcgt | 1560 |
| ggagaccctc tccagacacg ctgccccaga cctgcagcct tcaggcctct gttgctgacc | 1620 |
| tggctgttag gaatgactgc ttttgccgt tttcttttcg ttaccttct gggttgtcta | 1680 |
| acgtcttctc ccctctctcc cagggcacct tctctctgat tattgaagct ctccacacag | 1740 |
| attctcctga tgacctcgca acaggtaaaa acaaaaccca aacccaaaa ctgctttccc | 1800 |
| cagttaatag cattggactt tgcccaccca tccccagcc aaacccggac agctttcatt | 1860 |
| ctgcacgtgc cccagaaagt tcaggtgga gcagcttggg cctccttccc gtgctgaatg | 1920 |
| tctcggccca ccccgctct gtcccgagtc acagggttct cgttcagaac caaccaggag | 1980 |
| catcttctcc ccgtagaaaa cccagaaaga ctcatcagcc gcctggccac ccagaggcac | 2040 |
| ctgacggtgg gcgaggagtg gtcccaggac ctgcacagca gcggccgcac ggacctcaag | 2100 |
| tactcctacc gcttcgtgtg tgacgaacac tactacggag agggctgctc cgttttctgc | 2160 |
| cgtccccggg acgatgcctt cggccacttc acctgtgggg agcgtgggga gaaagtgtgc | 2220 |
| aaccctggct ggaaagggcc ctactgcaca gagcgtgagt ctctgggaag caccgctgg | 2280 |
| ctcactcgtc cacgaacacg gaccgcgcgc agggacgggg cttcctgagc cacggggggc | 2340 |
| ttgggactgt agagatgttc tggtggggaa actgaggccc agaggacaga agtggattgc | 2400 |
| tataagtcac agctcgtcag tgggggggtt ggggtcaacg cagacatttt aacatcccag | 2460 |
| gctgtgttta tccactatcg gaactgcctt tcttaatcag ggaggatttt agagacaggg | 2520 |
| ccaggggtca ggaagtaaag ccagtgctac ccccagggtg tgtgtattag agaggagag | 2580 |
| gaggaaggaa gggaggaaca cagagagagc ttgtgtgtca gggcaccat ttcaacccga | 2640 |
| gttcccagtg ctgaacagc atcacactgg gaaacgttcc attttctctc tggagctggt | 2700 |
| gtgcttgacc tctctggagc aaacgccttt ccggatactc cctgtgacac gcactgtcta | 2760 |
| tgctggccag agagcaggct ttcactcctg tgggctgctg aggccaggtc tccaaggcct | 2820 |
| gtgtgggcga ggggtgcaca gccccgtctg gcttgaatgc tcaggcagca ccttgtctgg | 2880 |
| agaagcaatg tcttcccaat agtgacagag gctctacctg cctcttatta ggtattgatg | 2940 |
| tgtcaatgtc atggcaggca ggtgactagg gcagggttgg ggccgtgctg gctcctggtt | 3000 |
| ctggctcatg ggaccctcag gagccctctc tccagctgac tgaggcctcg cctgcacgcc | 3060 |
| tggccgtccc agcccattgg taccggattt ctctacagct ggggattggg taggtcctgg | 3120 |
| agctgcccag aaactccagg gaactgtcat tctccttcct tggaactgga caaccttgga | 3180 |
| gagggctct gggaggccca gaacctctgg caggagctgg gtagtgcctg gggttgaggg | 3240 |

```
tgggtcttcc cattcactga gtgccttgat gtccttgctc cttagcttcc caaattccct    3300
ccggaactta ctgagctcct tctaagcttt gccttggcct gaactggttc tggggaaaaa    3360
caaaaaaaca aaaacaact tgtggagctg cttgttaatg agtttcataa ccaggcagca     3420
agagccagct ccaagcctca agcccactgt ctactccctg ccctgcggga gcctctggcc    3480
agtctgctgc ctcccaccct tcctccctgc ctctcttcac cacagggtag ccagaaactt    3540
aaactttttt cttcaaacac tgaagtctct ccccgccccc agctcgcgcg tgccatagat    3600
tagatctctc cggggatagg cgcagggaca cccgccggct cccattggcg aaggggtgc     3660
gtgtgcgtgt gtgtgtgtgt gtgtgtgtgt acacgcgagg ggtgtgtgtg aggaggtggg    3720
gccgggggcg cggggggaggc cggcattgtt gcgctgggc agctgccgtg gaggacagac    3780
aatggagcag ctgtcctgcc ctggcaccct gcataccagc tgtccactct tatctgcaca    3840
cacactttct gggatattaa gaggtggagc tttgtgcaca gaattgggaa gtggggggagg   3900
aggaggggga agacttctga ccctctctta gaagaaaagg ggatagggtg ggggtggggg    3960
cttccgagag ccctttttgtc cttgagcccc tgtgttaaga agaatgctca tcccagggc    4020
tgagtcaagt cccaggctac taggcagggg ggtcagtcct ccacaacctg ggaagattaa    4080
ctcagctggg atttgctgac tgaagccggc gagttgtgtc ctggcccaa gggcggcagc    4140
cctgttggga cgtacttggc gtgggggcttg accctgtttt cctttgctt gtagcgatct    4200
gcctgcctgg atgtgatgag cagcatggat tttgtgacaa accagggggaa tgcaagtaag   4260
tctgcacaag gtggtgtttt gttttgttgc cttttcttgt tatcttttca cagctggtgt    4320
atttgtaaaa acagccctag gtgatcattc gaaaaactcc agtaagattg attgaacagg    4380
gggccgtttt ctcatgtttc tacttaatca atgtttggca gcatgtaagg tcatggagtt    4440
gtcattcgtc taagcccctt aacggctatg agaatttaca gatagtagtt taaaaagagt    4500
tggcacagga aatgatagta tagttcaatg gttctcaaat gttgcctcat cctagaatca    4560
ctcagggagt gattttgag atgctgacac tggtgctgcc ctaacaccca agaagccaga     4620
acctctggtg gggcccaggc ccaggctgca gctcccaagg tgacccagtg ttctgctaat    4680
ctggagaacc agaggctcac tggtgctgcg ggaagatggt ttctagggtg agaatgtcca    4740
ctgcaaagcc agcaacagtc aacgtccatc tgagtcttct gctttctcc aaggtgcaga    4800
gtgggctggc agggccggta ctgtgacgag tgtatccgct atccaggctg tctccatggc    4860
acctgccagc agccctggca gtgcaactgc caggaaggct ggggggggcct tttctgcaac   4920
cagggtaagc cttctctccc tgaggcagcc tgctccctcc agagcagccc tggacttccc    4980
tggctgtttg atcactggaa aaataaagtc ttcctgcatt tgatgtcgag cttcctatct    5040
cctactttc ctgtccccac ccttcacaga cctgaactac tgcacacacc ataagccctg     5100
caagaatgga gccacctgca ccaacacggg ccaggggagc tacacttgct cttgccggcc    5160
tgggtacaca ggtgccacct gcgagctggg gattgacgag tgtgaccca gcccttgtaa     5220
gaacggaggg agctgcacgg tgagtcgag gctccatggc atctcacccg gaagctgggg    5280
tgccctggtg ttgaatggag tgtgtgggct ccttggagca actttggaaa gccttttctg    5340
acctctccat cgtgtaggat ctcgagaaca gctactcctg tacctgccca cccggcttct    5400
acggcaaaat ctgtgaattg agtgccatga cctgtgcgga cggcccttgc tttaacgggg    5460
gtcggtgctc agacagcccc gatgagggt acagctgccg ctgccccgtg gctactccg     5520
gcttcaactg tgagaagaaa attgactact gcagctcttc accctgttct aatggtaagg    5580
```

```
gggcagctgg tgattgctca gagactcggg cgagcggtca atactgaggt ggcattaaaa    5640
acaagcattt gtgagtgacc tcgagtttat gaatcacttt tatccagacc gccaggaatt    5700
ctcgatggaa actctatctt tgagtctgga aaggcctggg gaatgagaga ggccagggca    5760
tttgttatga agttctctgt ggaaacctag accaagcagt gaatgacttg ctcagggcca    5820
caaggtgctt cgggcacctg cggccgcctg aggttcagta agtgatgccc acaggtgccg    5880
gccactccag cttgggagga tggcccagct gtgtggccac ccagcacagt agttgggggt    5940
gtccctgagt gaggacagag agcctcctgc tagcagcgag gggctggctg cccaaaggag    6000
acacacagca aggagagctg ggccccagat gtgccggagc attccggaat ggtcatcctt    6060
cccctccctc cctcccctgt tgtcagtgcc tgctcctctc acttgctgtg taactgtggg    6120
caaggacacc ctcgttaagc ctcagtttcc ccatctgaaa cctgggtcga gtggcacatg    6180
ctcttgcccg gctgttgtgg cgactaatgc agccaccaga gtgttctgca cagcgcctgt    6240
ccagatgctg gccgtgtggt ttctgacttg tagagctaga cctggacacc tctcgtattt    6300
gaggtcctaa accatgtcac cttgcgctgt ggactcattc aggccacaga ctgtctttgg    6360
tttgtctggt ttctacagtg tcagacagat agatgcttca gagtgacttt ttggtgaaca    6420
aacctacgag gagacacgtg atgttcatgt ccctgtgttc caggtgccaa gtgtgtggac    6480
ctcggtgatg cctacctgtg ccgctgccag gccggcttct cggggaggca ctgtgacgac    6540
aacgtggacg actgcgcctc ctccccgtgc gccaacgggg gcacctgccg ggatggcgtg    6600
aacgacttct cctgcacctg cccgcctggc tacacgggca ggaactgcag tgcccccgtc    6660
agcaggtgcg agcacgcacc ctgccacaat ggggccacct gccacgagag gggccaccgc    6720
tatgtgtgcg agtgtgcccg aggctacggg ggtcccaact gccagttcct gctccccgag    6780
ctgcccccgg gcccagcggt ggtggacctc actgagaagc tagagggcca gggcgggcca    6840
ttcccctggg tggccgtgtg cgccggggtc atccttgtcc tcatgctgct gctgggctgt    6900
gccgctgtgg tggtctgcgt ccggctgagg ctgcagaagc accggccccc agccgacccc    6960 tgccggggg agacggagac catgaacaac ctggccaact gccagcgtga aaggacatc    7020 tcagtcagca tcatcggggc cacgcagatc aagaacacca caagaaggc ggacttccac    7080 ggggaccaca cgccgacaa gaatggcttc aaggcccgct acccagcggt ggactataac    7140
ctcgtgcagg acctcaaggg tgacgacacc gccgtcaggg acgcgcacag caagcgtgac    7200
accaagtgcc agccccaggg ctcctcaggg gaggagaagg ggaccccgac cacactcagg    7260
gggtgcgtgc tgcgggccgg gcatcaggag ggggtacctg gggggtgtct tcctggaacc    7320
actgctccgt ttctcttccc aaatgttctc atgcattcat tgtggatttt ctctattttc    7380
cttttagtgg agaagcatct gaaagaaaaa ggccggactc gggctgttca acttcaaaag    7440
acaccaagta ccagtcggtg tacgtcatat ccgaggagaa ggatgagtgc gtcatagcaa    7500
ctgaggtcag tgcaggcagc agccgctccc tcctcctcgg catgggagca cctgaagctg    7560
gagcacggga atcggtctca ggctaacttc ccatttgtct tgtggccccc caggtgtaaa    7620
atggaagtga gatggcaaga ctcccgtttc tcttaaaata gtaaaattc caaggatata    7680 tgccccaacg aatgctgctg aagaggaggg aggcctcgtg gactgctgct gagaaaccga    7740
gttcagaccg agcaggttct cctcctgagg tcctcgacgc ctgccgacag cctgtcgcgg    7800
cccggccgcc tgcggcactg ccttccgtga cgtcgccgtt gcactatgga cagttgctct    7860
taagagaata tatatttaaa tgggtgaact gaattacgca taagaagcat gcactgcctg    7920
agtgtatatt ttggattctt atgagccagt cttttcttga attagaaaca caaacactgc    7980
```

```
cttattgtc cttttgata cgaagatgtg ctttttctag atggaaaaga tgtgtgttat   8040
tttttggatt tgtaaaaata tttcatga tatctgtaaa gcttgagtat tttgtgatgt    8100 tcgttttta taattaaat tttggtaaat atgtacaaag gcacttcggg tctatgtgac    8160 tatattttt tgtatataaa tgtatttatg gaatattgtg caaatgttat ttgagttttt   8220
tactgttttg ttaatgaaga aattccttt taaaatattt ttccaaaata aatttatga    8280 atgacaacca gaaggcgtag ttacttggct ttgccttaga gcggaggtgt gctcactcac   8340
ctgcggcccg cgaggctgag ggcagaggtg gccttggtgt                         8380

<210> SEQ ID NO 9
<211> LENGTH: 21
<212> TYPE: DNA
<213> ORGANISM: Homo sapiens

<400> SEQUENCE: 9
tcccccaact actccaacga c                                             21

<210> SEQ ID NO 10
<211> LENGTH: 17
<212> TYPE: DNA
<213> ORGANISM: Homo sapiens

<400> SEQUENCE: 10
ccctcccaac gccactg                                                  17

<210> SEQ ID NO 11
<211> LENGTH: 233
<212> TYPE: DNA
<213> ORGANISM: Homo sapiens

<400> SEQUENCE: 11
tcccccaact actccaacga cttgaactcc atggccggct cgccggtctc atcctactcg   60
tcggacgagg gctcttacga cccgctcagc cccgaggagc aggagcttct cgacttcacc   120
aactggttct gagggctcg gcctggtcag gccctggtgc gaatggactt tggaagcagg    180
gtgatcgcac aacctgcatc tttagtgctt tcttgtcagt ggcgttggga ggg          233

<210> SEQ ID NO 12
<211> LENGTH: 21
<212> TYPE: DNA
<213> ORGANISM: Homo sapiens

<400> SEQUENCE: 12
gagaggcggc taaggtgttt g                                             21

<210> SEQ ID NO 13
<211> LENGTH: 20
<212> TYPE: DNA
<213> ORGANISM: Homo sapiens

<400> SEQUENCE: 13
ctggtgtaga cggggatgac                                               20

<210> SEQ ID NO 14
<211> LENGTH: 150
<212> TYPE: DNA
<213> ORGANISM: Homo sapiens

<400> SEQUENCE: 14
```

-continued

```
ccttggtgac caatgccagc cagagtcctg cggggtggg cccggccctc cctggatctc    60
ctccctcctc ccaggggttc agatgtggtg gggtagggcc ctggaagtct cccaggtctt   120
ccctccctcc tctgatggat ggcttgcagg                                    150
```

<210> SEQ ID NO 15
<211> LENGTH: 19
<212> TYPE: DNA
<213> ORGANISM: Homo sapiens

<400> SEQUENCE: 15

```
ccttggtgac caatgccag                                                 19
```

<210> SEQ ID NO 16
<211> LENGTH: 19
<212> TYPE: DNA
<213> ORGANISM: Homo sapiens

<400> SEQUENCE: 16

```
cctgcaagcc atccatcag                                                 19
```

<210> SEQ ID NO 17
<211> LENGTH: 150
<212> TYPE: DNA
<213> ORGANISM: Homo sapiens

<400> SEQUENCE: 17

```
ccttggtgac caatgccagc cagagtcctg cggggtggg cccggccctc cctggatctc    60
ctccctcctc ccaggggttc agatgtggtg gggtagggcc ctggaagtct cccaggtctt   120
ccctccctcc tctgatggat ggcttgcagg                                    150
```

<210> SEQ ID NO 18
<211> LENGTH: 21
<212> TYPE: DNA
<213> ORGANISM: Homo sapiens

<400> SEQUENCE: 18

```
tcctgatgac ctcgcaacag a                                              21
```

<210> SEQ ID NO 19
<211> LENGTH: 20
<212> TYPE: DNA
<213> ORGANISM: Homo sapiens

<400> SEQUENCE: 19

```
acacacgaag cggtaggagt                                                20
```

<210> SEQ ID NO 20
<211> LENGTH: 145
<212> TYPE: DNA
<213> ORGANISM: Homo sapiens

<400> SEQUENCE: 20

```
tcctgatgac ctcgcaacag aaaacccaga aagactcatc agccgcctgg ccacccagag    60
gcacctgacg gtgggcgagg agtggtccca ggacctgcac agcagcggcc gcacggacct   120
caagtactcc taccgcttcg tgtgt                                         145
```

<210> SEQ ID NO 21
<211> LENGTH: 20
<212> TYPE: DNA
<213> ORGANISM: Artificial

```
<220> FEATURE:
<223> OTHER INFORMATION: ASCL1_Forward primer

<400> SEQUENCE: 21
ctcaacttca gcggctttgg                                              20

<210> SEQ ID NO 22
<211> LENGTH: 20
<212> TYPE: DNA
<213> ORGANISM: Artificial
<220> FEATURE:
<223> OTHER INFORMATION: ASCL1_Reverse primer

<400> SEQUENCE: 22
gctcgccggt ctcatcctac                                              20

<210> SEQ ID NO 23
<211> LENGTH: 22
<212> TYPE: DNA
<213> ORGANISM: Artificial
<220> FEATURE:
<223> OTHER INFORMATION: HES1_Forward primer

<400> SEQUENCE: 23
atggagaaaa attcctcgtc cc                                           22

<210> SEQ ID NO 24
<211> LENGTH: 23
<212> TYPE: DNA
<213> ORGANISM: Artificial
<220> FEATURE:
<223> OTHER INFORMATION: HES1_Reverse primer

<400> SEQUENCE: 24
ttcagagcat ccaaaatcag tgt                                          23

<210> SEQ ID NO 25
<211> LENGTH: 19
<212> TYPE: DNA
<213> ORGANISM: Artificial
<220> FEATURE:
<223> OTHER INFORMATION: HES6_Forward primer

<400> SEQUENCE: 25
ccttggtgac caatgccag                                               19

<210> SEQ ID NO 26
<211> LENGTH: 19
<212> TYPE: DNA
<213> ORGANISM: Artificial
<220> FEATURE:
<223> OTHER INFORMATION: HES6_Reverse primer

<400> SEQUENCE: 26
cctgcaagcc atccatcag                                               19

<210> SEQ ID NO 27
<211> LENGTH: 21
<212> TYPE: DNA
<213> ORGANISM: Artificial
<220> FEATURE:
<223> OTHER INFORMATION: DLL1_Forward primer

<400> SEQUENCE: 27
tcctgatgac ctcgcaacag a                                            21
```

-continued

```
<210> SEQ ID NO 28
<211> LENGTH: 20
<212> TYPE: DNA
<213> ORGANISM: Artificial
<220> FEATURE:
<223> OTHER INFORMATION: DDL1_Reverse primer

<400> SEQUENCE: 28
acacacgaag cggtaggagt                                               20
```

METHOD FOR DIAGNOSIS OF GLIOMA: DISTINGUISHING BETWEEN PROGRESSIVE AND DE NOVO TYPES

RELATED APPLICATIONS

The present patent document claims the benefit of the filing date of Indian Patent Application No. 1975/DEL/2005, filed Jul. 26, 2005, which is hereby incorporated by reference.

BACKGROUND

1. Technical Field

The present invention relates to a method for identifying the type of glioblastoma multiforme in mammals, preferably human subjects. More particularly, it relates to a kit for characterizing progressive glioma in mammals, preferably human subjects. More particularly, it relates to a kit for distinguishing primary and secondary glioblastoma multiforme in mammals, preferably human subjects.

2. Background Information

Gliomas are the most common primary brain tumors and occur at an incidence of almost 12 per 100,000 people (Landis et al., 1999). Diffuse astrocytoma may be classified (as per WHO classification) as low-grade diffuse (DA; Grade II), anaplastic (AA; Grade III) and glioblastoma multiforme (Grade IV; GBM), in the order of increasing malignancy (Mischel et al., 2001). Currently, these classifications are based on the observed histopathological characteristics of the tumor, which are sometimes subjective and inconsistent. GBM constitutes more than 80% of malignant gliomas (DeAngelis et al., 2001) and patients with GBM have a median survival of less than one year. Current treatments, including surgery, radiation therapy, and chemotherapy, unfortunately have not changed the natural history of these incurable neoplasms; and the prognosis of patients with GBMs has not improved significantly in the past 30 years (Davis et al., 1998). To find new diagnostic and therapeutic strategies, a better understanding of the biological pathway(s) leading to glial tumorigenesis is warranted.

Astrocytoma development is known to involve accumulation of a series of genetic alterations (Nagane et al., 1997) similar to other cancers. Identification of many of the genes involved in astrocytoma development, using standard molecular approaches, has helped to understand the process of astrocytomagenesis and progression (Louis and Gusella, 1995). Frequent amplification of epidermal growth factor receptor (EGFR) (Hill et al., 1999; Brock and Bower, 1997), platelet derived growth factor receptor (PDGFR) (Hermanson et al., 1992; Hermanson et al., 1996; Maxwell et al., 1990; Westermark et al., 1995; Fleming et al., 1992), amplification of chromosome 12q region, which carries the cdk4 gene (Nagane et al., 1997; Hill et al., 1999) and alterations in chromosomes 1p, 9p, 10, 17p, 19q, and 22q have frequently been found in these tumors. In addition, mutations in the tumor suppressor gene p53 were found to be associated with chromosome 17p alterations in low grade and progressive astrocytoma (Maher et al., 2001; Phatak et al., 2002). Inactivation of the cdk inhibitor p16 INK4a residing in chromosome 9p, is very common in sporadic astrocytoma, occurring in 50-70% of high-grade gliomas and 90% of GBM cell lines (James et al., 1991; Olopade et al., 1992). LOH in chromosome 10 is one of the most frequent alterations in GBM and is accompanied by the loss of PTEN/MMAC gene (Hill et al., 1999; Li et al., 1997).

GBMs are of two types: primary GBM (de novo type), which manifests in older patients (mean age: 55 yrs) as an aggressive, highly invasive tumor, usually without any evidence of prior clinical disease after a short clinical history of less than 3 months; secondary GBM (progressive type) is usually seen in younger patients (mean age: 40 yrs) and develops more slowly by malignant progression from diffuse (WHO grade II) or anaplastic astrocytoma (WHO grade III). Although some differences in the genetic lesions between these two GBMs have been identified, they are not sufficient enough to be used as differentiating markers considering the fact that the two types of GBMs have comparable clinical, genetic and biological characteristics (Kleihues et al., 2002). However, it is likely that these subtypes would respond differently to specific novel therapies as they are developed in the future (Kleihues and Ohgaki, 1999).

Previously, cancer classification has been based primarily on the morphological appearance of tumor cells. But this has serious limitations, because tumors with similar histopathgological appearance can follow significantly different clinical courses and show different responses to therapy. For example, based on histopathological appearance, astrocytoma grade IV cannot consistently be distinguished from astrocytoma grade III.

Immunophenotyping for brain tumors has defined and refined diagnosis, e.g., distinguishing oligoastrocytoma from malignant astrocytomas, and high-grade from low-grade astrocytomas. However, differential protein expression (GFAP, vimentin, synaptophysin, nestin) has not helped to improve therapeutic approaches. Prediction of transitions from low- to high-grade astrocytomas is difficult to make with currently available markers (De Girolami et al., 1994).

However, these and other molecular markers currently in use are not capable of unambiguously identifying the subtypes of GBM. Mutations in p53 gene are reported to be associated with about 50% of grade II/III astrocytomas and secondary glioblastomas, but are seen only in 10-20% of primary glioblastoma (Campomenosi et al., 1996; Watanabe et al., 1997; Schmidt et al., 2002). Similarly, Epidermal growth factor receptor (EGFR), another marker routinely used in the classification of GBMs is found to be amplified in only 40% of all primary GBM cases and is rarely reported in secondary GBMs (Frederick et al., 2000).

Thus, secondary GBMs, which progress from less malignant grades, cannot readily be distinguished from progressive GBMs by current histopathological methods.

Despite all this information about glioma, our understanding of astrocytoma development is not sufficient enough to improve prognosis for GBM patients. A more global, systematic understanding of expression patterns of various genes and their downstream gene products in astrocytoma will hopefully provide new diagnostic and therapeutic targets. Towards this, a number of studies have reported the gene expression profile of astrocytoma (Liau et al., 2000; Sallinen et al., 2000; Rickman et al., 2001; Ljubimova et al., 2001; Watson et al., 2001; Tanwar et al., 2002; Fathallah-Shaykh et al., 2002; Nutt et al., 2003; Wang et al., 2003; Godard et al., 2003).

It is also desirable to be able to target specific therapeutic modalities to pathogenetically distinct tumor types to maximize efficacy and minimize toxicity to the patient. (Golub et al., 1999; Kudoh et al., 2000). Previously, cancer classification has been based primarily on the morphological appearance of tumor cells. But this has serious limitations, because tumors with similar histopathgological appearance can follow significantly different clinical courses and show different responses to therapy. For example, based on histopathological appearance, astrocytoma grade IV cannot consistently be distinguished from astrocytoma grade III.

Immunophenotyping for brain tumors has defined and refined diagnosis, e.g., distinguishing oligoastrocytoma from malignant astrocytomas, and high-grade from low-grade astrocytomas. However, differential protein expression (GFAP, vimentin, synaptophysin, nestin) has not helped to improve therapeutic approaches. Prediction of transitions from low- to high-grade astrocytomas is difficult to make with currently available markers (De Girolami et al., 1994).

Tews et al. reported that immunohistochemical detection of various cancer-associated markers failed to reveal significant differential expression patterns among primary and secondary glioblastomas and precursor tumors; there was also no intra-individual constant expression pattern during glioma progression or correlation with malignancy (Tews and Nissen, 1998-99). In contrast, class prediction for leukemia has been described based on monitoring gene expression profiles with DNA microarrays (Golub et al., 1999).

But no class prediction capability, based on gene expression profiles, has been available heretofore for classifying gliomas to allow for optimizing treatment regimens. The molecular markers currently in use are not capable of unambiguously identifying the subtypes of GBM. Mutations in p53 gene are reported to be associated with about 50% of grade II/III astrocytomas and secondary glioblastoma, but are seen only in 10-20% of primary glioblastoma (Campomenosi et al., 1996: Watanabe et al., 1997: Schmidt et al., 2002). Similarly, Epidermal growth factor receptor (EGFR), another marker routinely used in the classification of GBMs is found to be amplified in only 40% of all primary GBM cases and is rarely reported in secondary GBMs (Frederick et al., 2000). Clearly, these markers used alone or in combination lack the ability to robustly classify gliomas into the progressive and de novo types. The immunohistochemical determination of the proliferative nature of tumors with the monoclonal antibody MIB-1 against Ki-67, a nuclear antigen, has been used widely for establishing the grade for many tumors (Schiffer at al., 1997, Di et al, 1997). Thus, secondary GBMs, which progress from less malignant grades, cannot readily be distinguished from de novo GBMs by current histopathological methods.

Therefore, it is also a desideratum to be able to predict the subtype of glioblastoma multiforme and, thus, to be able to administer appropriate treatment. These and other benefits are provided by the present invention.

SUMMARY OF THE INVENTION

The main object of the present invention is to provide a method for identifying the type of glioblastoma multiforme in mammals, preferably human subjects.

Another object of the present invention is to provide a kit for characterizing progressive glioma in mammals, preferably human subjects.

Further, object of the present invention is to provide a kit for distinguishing primary and secondary glioblastoma multiforme in mammals, preferably human subjects.

The present invention deals with a method for identifying the type of glioblastoma multiforme in mammals preferably human subjects the expression level of a single or combination of genes selected from notch signaling pathway such as Achaete-scute complex-like 1 (ASCL1) having accession number NM_004316, Hairy and Enhancer of Split 1 (HES1) having accession number NM_0055246, Hairy and Enhancer of Split 6 (HES 6) having accession number: NM_018645 and Delta-like 1 (DLL1) having accession number NM_005618 in a test sample of brain tissue cells obtained from a mammals preferably human subject and in a control sample of known normal brain tissue cells, wherein the higher level of expression of Achaete-scute complex-like 1, Hairy and Enhancer of Split 6 and Delta-like 1 in the test sample indicates the presence of secondary glioblastoma multiforme as compared to the control sample and a lower level of expression of Hairy and Enhancer of Split 1 in the test sample as compared to the control sample indicates the presence of secondary glioblastoma multiforme in a mammals preferably human subject from which the test sample is obtained. It also deals with a kit for characterizing progressive glioma in mammals, preferably human subjects, and a kit for distinguishing primary and secondary glioblastoma multiforme in mammals, preferably human subject.

Note that grade II diffuse astrocytoma, grade III anaplastic astrocytoma, secondary GBM but not Primary GBM samples are positive for ASCL1 staining.

Figure 3:
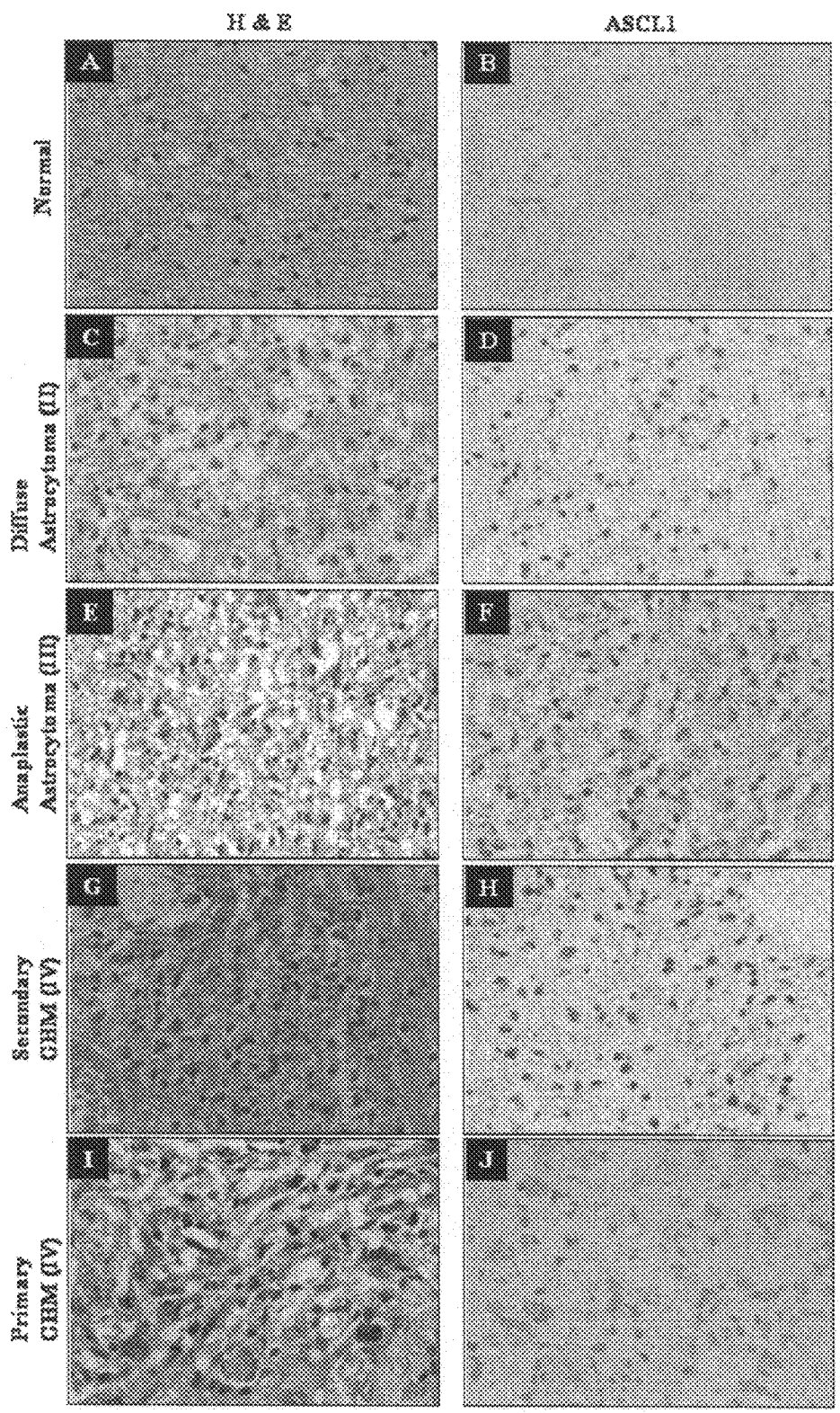

FIG. 3 represents Immunohistochemical validation of ASCL1 overexpression in progressive astrocytoma. Sections from normal brain (A and B), grade II diffuse astrocytoma (C and D), grade III anaplastic astrocytoma (E and F), secondary GBMs (G and H) and Primary GBMs (I and J) were stained with H & E (A, C, E, G and I) and for ASCL1 (B, D, F, H and J).

Note that grade II diffuse astrocytoma, grade III anaplastic astrocytoma, secondary GBM but not Primary GBM samples are positive for ASCL1 staining.

DETAILED DESCRIPTION OF THE DRAWINGS AND THE PRESENTLY PREFERRED EMBODIMENTS

Accordingly, the present invention provides a method for identifying the type of glioblastoma multiforme in mammals preferably human subjects, comprising determining the expression level of a single or combination of genes selected from notch signaling pathway such as Achaete-scute complex-like 1 (ASCL1) having accession number NM_004316, Hairy and Enhancer of Split 1 (HES1) having accession number NM_0055246, Hairy and Enhancer of Split 6 (HES 6) having accession number: NM_018645 and Delta-like 1 (DLL1) having accession number NM_005618 in a test sample of brain tissue cells obtained from a mammals preferably human subject and in a control sample of known normal brain tissue cells, wherein the higher level of expression of Achaete-scute complex-like 1, Hairy and Enhancer of Split 6 and Delta-like 1 in the test sample indicates the presence of secondary glioblastoma multiforme as compared to the control sample and a lower level of expression of Hairy and Enhancer of Split 1 in the test sample as compared to the control sample indicates the presence of secondary glioblastoma multiforme in a mammals preferably human subject from which the test sample is obtained.

In an embodiment of the present invention, the expression level of said genes is determined by checking the level of RNA transcripts of the said genes by employing an oligonucleotide in nucleic acid-based detection methods such as in situ hybridisation, RT-PCR analysis etc. or optionally the expression level of said genes is determined by checking the level of respective proteins of said genes by employing an antibody in protein-based detection methods such as immunohistochemistry, Western blot analysis etc.

In another embodiment of the present invention, the presence of secondary glioblastoma multiforme is identified using the said genes in combination with known markers selected from the group consisting of EGFR, p53, Ki-67 etc.

Further, the present invention provides a kit for characterizing progressive glioma in a mammals preferably human subject, wherein the said kit comprising:
  a) reagent capable of specifically detecting the presence or absence of the combination of genes of the Notch signaling pathway such as Achaete-scute complex-like 1, Hairy and Enhancer of Split 1, Hairy and Enhancer of Split 6 and Delta-like 1;
  b) instructions for using said kit for characterizing progressive glioma in said mammals, preferably human subject.

In an embodiment of the present invention, the reagent used comprises a nucleic acid probes selected from the group comprising of probe of SEQ ID No. 14 complementary to mRNAs of the hairy and enhancer of split 1 (HES) gene of SEQ ID No. 1 having accession no. NM_005524, probe of SEQ ID No. 11 complementary to mRNAs of the achaete-scute complex like 1 (ASCL1) gene of SEQ ID No. 3 having accession no. NM_004316, probe of SEQ ID No. 17 complementary to mRNAs of the hairy and enhancer of split 6 (HES6) gene of SEQ ID No. 5 having accession no. NM_018645, probe of SEQ ID No. 20 complementary to mRNAs of the delta-like 1 (DLL1) gene having accession no. NM_005618 of the Notch signaling pathway.

In another embodiment of the present invention, the reagent used comprises an antibody that specifically binds to proteins encoded by the genes of the Notch signaling pathway selected from the group comprising of as Achaete-scute complex-like 1 (ASOL1) having accession number NM_004316, Hairy and Enhancer of Split 1 (HES1) having accession number NM_005524, Hairy and Enhancer of Split 6 (HES 6) having accession number: NM_018645 and Delta-like 1 (DLL1) having accession number NM_005618.

The present invention also provides a kit for distinguishing primary and secondary glioblastoma multiforme in a mammals preferably human subject, wherein the said kit comprising:
  a) a reagent capable of specifically detecting the presence or absence of the combination of said genes such as Achaete-scute complex-like 1, Hairy and Enhancer of Split 1, Hairy and Enhancer of Split 6, and Delta-like 1;
  b) instructions for using said kit for characterizing secondary glioblastoma multiforme in said mammals, preferably human subject.

In an embodiment of the present invention, the reagent used comprises a nucleic acid probes selected from the group comprising of probe of SEQ ID No. 14 complementary to mRNAs of the hairy and enhancer of split 1 (HES) gene of SEQ ID No. 1 having accession no. NM_005524, probe of SEQ ID No. 11 complementary to mRNAs of the achaete-scute complex like 1 (ASCL1) gene of SEQ ID No. 3 having accession no. NM_004316, probe of SEQ ID No. 17 complementary to mRNAs of the hairy and enhancer of split 6 (HES6) gene of SEQ ID No. 5 having accession no. NM_018645, probe of SEQ ID No. 20 complementary to mRNAs of the delta-like 1 (DLL1) gene having accession no. NM_005618 of the Notch signaling pathway.

In another embodiment of the present invention, the said reagent comprises an antibody that specifically binds to proteins encoded by the said genes of the Notch signaling pathway selected from the group comprising of as Achaete-scute complex-like 1 (ASCL1) having accession number NM_004316, Hairy and Enhancer of Split 1 (HES1) having accession number NM_005524, Hairy and Enhancer of Split 6 (HES 6) having accession number: NM_018645 and Delta-like 1 (DLL1) having accession number NM_005618.

Gliomas include any malignant glial tumor, i.e., a tumor derived from a transformed glial cell. A glial cell includes a cell that has one or more glial-specific features, associated with a glial cell type, including a morphological, physiological and/or immunological feature specific to a glial cell (e.g. astrocytes or oligodendrocytes), for example, expression of the astroglial marker fibrillary acidic protein (GFAP) or the oligodendroglial marker O4. Gliomas include, but are not limited to, astrocytoma grade II, anaplastic astrocytoma grade III, astrocytoma with oligodendrogliomal component, oligodendroglioma, and glioblastoma multiforme (GBM; astrocytoma grade IV).

The inventive method involves collecting or otherwise obtaining a sample of a bodily substance derived from the mammals preferably human subject, which sample contains mammals preferably human nucleic acid or protein originating from the subject, and quantitatively or semi-quantitatively detecting therein over expression or lack thereof of the combination of genes of the Notch pathway including, but not limited to, Achaete-scute complex-like 1, Hairy and Enhancer of Split 1, Hairy and Enhancer of Split 6 and Delta-like 1. This includes detection by means of measuring of proteins or specific nucleic acids, such as RNA or cDNA. A characteristic expression pattern of the said genes is diagnostic for the presence of different types of glioma.

The sample is preferably collected directly from the mammals, preferably human subject's body. Preferred and convenient substances for sampling include blood, lymph or plasma, cerebrospinal fluid, other biopsy sample of cellular material from brain tissue. Cellular material includes any sample containing mammals, preferably human cells, including samples of tissue, expressed tissue fluids (e.g., lymph or plasma) or tissue wash and the like. Tissue samples that can be collected include, but are not limited to, cell-containing material from the brain. This includes normal brain tissue, tumor tissue, tumor-adjacent tissue, and/or blood plasma from a site within the brain.

In accordance with the inventive methods, the tissue sample preferably contains cells that express a plurality of protein species and mRNA species, which proteins and/or mRNA species are detectably distinct from one another. "Obtaining" and "collecting" the sample are used interchangeably herein and encompass sampling, resecting, removing from in situ, aspirating, receiving, gathering, and/or transporting the tissue sample or a concentrate, sediment, precipitate, supernatant, filtrate, aspirate, or other fraction of any of these. For example, conventional biopsy methods are useful for obtaining the tissue sample. These include percutaneous biopsy, laparoscopic biopsy, surgical resection, tissue scrapes and swabs, sampling via stents, catheters, endoscopes, needles, surgical resection, and other known means. For example, to obtain a sample from inside the skull of the mammals preferably human subject; typically, Magnetic Resonance Imaging (MRI)-guided stereotactic techniques are employed, but other methods can be used.

The sample is alternatively derived from cultured mammals, preferably human cells, cell-free extracts, or other specimens indirectly derived from a subject's body, as well as from substances taken directly from a subject's body. Samples may be stored before detection methods are applied (for example nucleic acid amplification and/or analysis, or immunochemical detection) by well known storage means that will preserve nucleic acids or proteins in a detectable and/or analyzable condition, such as quick freezing, or a controlled freezing regime, in the presence of a cryoprotectant, for example, dimethyl sulfoxide (DMSO), trehalose, glycerol, or propanediol-sucrose. Samples may also be pooled before or after storage for purposes of amplifying the nucleic acids specific for the said genes for analysis and detection, or for purposes of detecting the respective proteins.

The sample is used immediately or optionally pre-treated by refrigerated or frozen storage overnight, by dilution, by phenol-chloroform extraction, or by other like means, to remove factors that may inhibit various amplification reactions. The level of expression in the sample for the said proteins or their messenger ribonucleic acid (mRNA) is then detected quantitatively or semi-quantitatively.

Polynucleotides specific for the said genes, including mRNA species, are determined by base sequence similarity or homology to known nucleotide sequences. Base sequence homology is determined by conducting a base sequence similarity search of a genomics data base, such as the GenBank database of the National Center for Biotechnology Information (NCBI; www.ncbi.nlm.nih.gov/BLAST/), using a computerized algorithm, such as PowerBLAST, QBLAST, PSI-BLAST, PHI-BLAST, gapped or ungapped BLAST, or the "Align" program through the Baylor College of Medicine server (www.hgsc.bcm.tmc.edu/seq_data) (Altchul, et al., 1997; Zhang and Madden, 1997; Madden et al., 1996; Altschul et al., 1990).

Preferably, polynucleotide sequences specific to the said genes, including an mRNA sequence, is at least 5 to 30 contiguous nucleotides long, more preferably at least 6 to 15 contiguous nucleotides long, and most preferably at least 7 to 10 contiguous nucleotides long. mRNA specific to any of the said genes can be, but is not necessarily, an mRNA species containing a nucleotide sequence that encodes a functional version of the said genes or fragments thereof. Also included among mRNAs specific to the said genes are splice variants.

Quantitatively or semi-quantitatively detecting the expression levels of mRNAs specific to the said genes or their proteins, or of other proteins or mRNA species of interest in accordance with the present invention, is done by any known method that provides a quantitative or semi-quantitative determination of expression. A "quantitative" detection method provides an absolute value for the amount or level of expression in comparison to a standard, which amount or level is typically a mole, mass, or activity value normalized in terms of a specified mass of protein, mass of nucleic acid, number or mass of cells, body weight, or the like. Additionally, the quantitative or absolute value is optionally normalized in terms of a specified time period, i.e., expression level as a rate. A "semi-quantitative detection method provides a unitless relative value for the amount or level of expression, for example, in terms of a ratio of expression in a given sample relative to a control, such as normal tissue or the expression of a selected "housekeeping" gene. The skilled artisan is aware of other examples of quantitative and semi-quantitative detection methods.

In accordance with the inventive methods, the expression level of the proteins encoded by the said genes is optionally detected by immunochemical means, such as, but not limited to, enzyme-linked immunosorbent assay (ELISA), immunofluorescent assay (IFA), immunoelectrophoresis, immunochromatographic assay or immunohistochemical staining, employing polyclonal or monoclonal antibodies or antibody fragments against the said gene products. Antibodies or antibody fragments that target the said proteins are available commercially or can be produced by conventional means.

Similarly, the expression levels of other proteins of interest, in accordance with the inventive methods, can be detected by conventional immunochemical means as described above. These proteins include, but are not limited to, Achaete-scute complex-like 1, Hairy and Enhancer of Split 1, Hairy and Enhancer of Split 6, and Delta-like 1.

Most preferably, quantitative or semi-quantitative detection of the expression level of mRNA species is accomplished by any of numerous methods of nucleic acid amplification (e.g., amplification of specific nucleic acid segments) in the form of RNA or cDNA, which RNA or cDNA amplification product is ultimately measured after amplification. The final amplification product of RNA or cDNA is measured by any conventional means, such as, but not limited to, densitometry, fluorescence detection, or any other suitable biochemical or physical assay system. Before amplification, it is preferable to extract or separate mRNA from genomic DNA in the sample and to amplify nucleic acids remaining in that fraction of the sample separated from the DNA, to avoid false positives that are caused by amplification of contaminating genomic DNA in the original specimen.

Histopathological means of classifying malignant tumors into grades are known for various kinds of malignant tumor, including gliomas (Cotran et al., 1994; Daumas-Duport et al., 1988).

Figure 1:
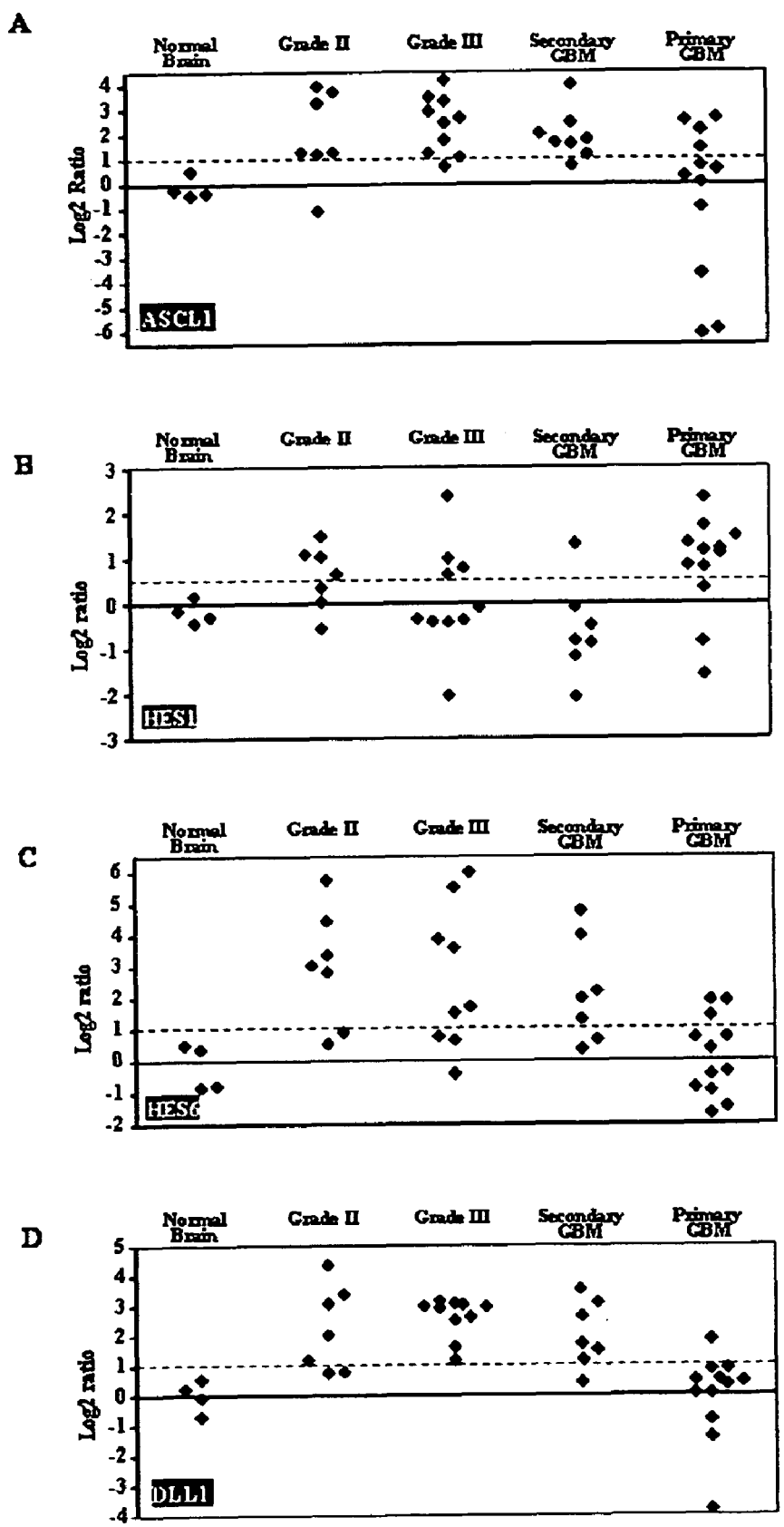
FIG. 1 represents Scatter-plots of differentially regulated notch pathway genes during astrocytoma: Log 2-transformed gene expression ratios obtained from real-time quantitative PCR analysis are plotted for ASCL1(A), HES1 (B), HES6 (C), and DLL1 (D). Each dot represents a data derived from one sample. A change in gene expression by 2 fold or more over its mean expression in normal brain sample was considered significant except in the case of HES1 where a cutoff of 1.5 fold was used. Fold change cutoffs are represented by dashed lines.

Primary and secondary GBMs are frequently indistinguishable with conventional histopathological methods, but using the inventive method, these types are readily distinguished, since secondary GBMs generally overexpress any or a combination of genes from the group consisting of, but not limited to, Achaete-scute complex-like 1, Hairy and Enhancer of Split 6, and Delta-like 1 and primary GBMs generally overexpress any or a combination of genes from the group consisting of, but not limited to, Hairy and Enhancer of Split 1 (See FIG. 1).

The second group contains the type that arises de novo and is more aggressive (primary GBMs), as described herein; the first group contains the type that progresses from lower grades and is less aggressive (secondary GBMs).

The foregoing descriptions of the methods of the present invention are only illustrative and by no means exhaustive. When these features of the present invention are employed, diagnostic and treatment decisions can be more appropriately optimized for the individual glioma patient, and the prospects for his or her survival can be enhanced.

Figure 2:
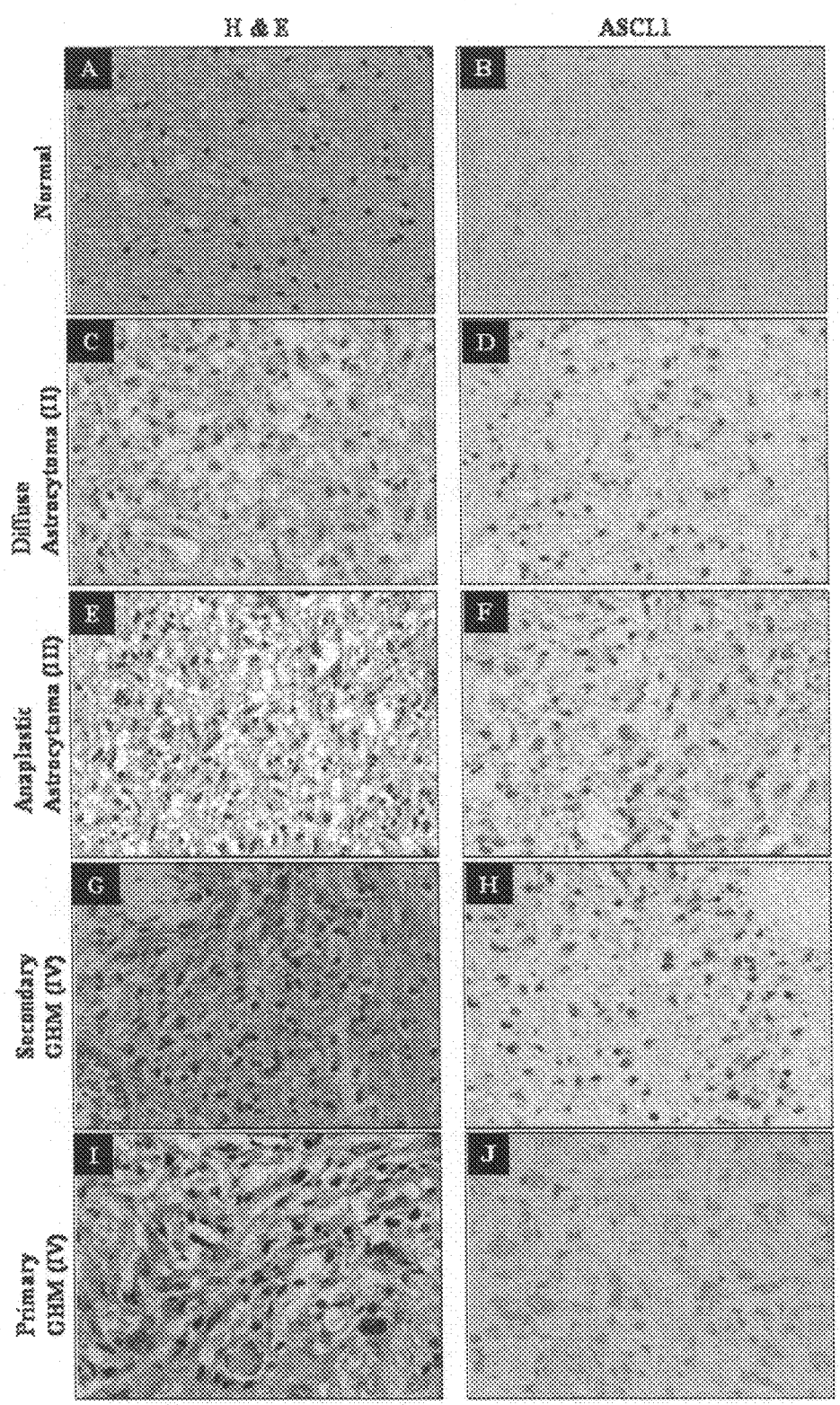
FIG. 2 represents Immunohistochemical validation of ASCL1 overexpression in progressive astrocytoma. Sections from normal brain (A and B), grade II diffuse astrocytoma (C and D), grade III anaplastic astrocytoma (E and F), secondary GBMs (G and H) and Primary GBMs (I and J) were stained with H & E (A, C, E, G and I) and for ASCL1 (B, D, F, H and J).

ASCL1 has been shown to be highly expressed in neuroendocrine cancers, medullary thyroid cancer (MTC) and small cell lung cancer (SCLC) (Ball et al., 1993). We found that ASCL1 to be upregulated in majority of grade II diffuse astrocytomas (85.71%; 6/7), grade III anaplastic astrocytoma (90%; 9/10) and secondary GBMs (87.5%; 7/8) (FIG. 1A). However, among primary GBMs, ASCL1 upregulation was seen only in 33.33% (4/12) of the samples (FIG. 1A). Increase in ASCL1 transcripts also correlated immunohistochemically with increased nuclear staining for ASCL1 in grade II diffuse astrocytoma (FIG. 2D), grade III anaplastic astrocytoma (FIG. 2F), and secondary GBM (FIG. 2H). Most of these samples also showed increased nuclear staining for p53, which is indicative of mutated p53 characterizing progressive astrocytomas and did not show staining for EGFR (Table 1). As expected, primary GBMs did not show detectable staining for ASCL1 (FIG. 2J). Majority of these tumors overexpressed EGFR whilst p53 immunoreactivity was noted in minimal number of cases (Table 1). Normal brain sections did not reveal immunoreactivity for ASCL1 (FIG. 2), p53 and EGFR (data not shown). Table 1 describes the details about various astrocytoma samples used in this study, their staining pattern for various markers and their clinical parameters. Since ASCL1 upregulation is seen in majority of secondary, but not in primary, GBMs. ASCL1 status could be used as a marker to differentiate secondary GBM from primary GBM. Mutations in p53 gene are associated with about 50% of grade II/III astrocytomas and secondary glioblastomas, but are seen only in 10-20% of primary glioblastoma (Campomenosi et al., 1996; Watanabe et al., 1997; Schmidt et al., 2002).

TABLE 1

ASCL1 expression characterizes progressive astrocytoma

| S No | Sample ID | Age of patient | Duration of symptoms (in months) | MIB-LI (%) | p53 | EGFR | ASCL1 | Status | Fold Change |
|---|---|---|---|---|---|---|---|---|---|
| \multicolumn{10}{c}{IV, Primary GBM} |
| 1 | 95 | 55 | 3 | 10 | + | + | − | ↓ | −1.95 |
| 2 | 122 | 61 | 2 | 16 | − | + | − | ↓ | −12.86 * |
| 3 | 242 | 57 | 1 | 20 | − | + | + | ↔ | 1.98 |
| 4 | 64 | 67 | 1 | 18.5 | + | + | − | ↓ | −67.68 |
| 5 | 65 | 70 | 6 | 18.5 | + | + | + | ↑ | 5.49 |
| 6 | 81 | 45 | 3 | 16.5 | − | + | − | ↔ | 1.47 |
| 7 | 61 | 50 | 3 | 18.5 | − | + | − | ↔ | 1.02 |
| 8 | 258 | 46 | 3 | 21 | − | + | + | ↑ | 6.27 |
| 9 | 75 | 25 | 0.5 | 32 | + | + | − | ↓ | −59.72 |
| 10 | 156 | 53 | 3 | 16 | − | + | + | ↑ | 4.44 |
| 11 | 94 | 58 | 3 | 18 | − | + | + | ↔ | 1.21 |
| 12 | 110 | 43 | 4 | 11.5 | + | + | − | ↑ | 2.65 |
| \multicolumn{10}{c}{IV, Secondary GBM} |
| 1 | 146 | 35 | 2 | 40 | + | + | + | ↑ | 15.99 |
| 2 | 195 | 43 | 3 | 28 | + | − | + | ↑ | 3.16 * |
| 3 | 197 | 18 | 4 | 13 | + | − | − | ↑ | 4.02 |
| 4 | 251 | 35 | 5 | 28 | + | − | + | ↑ | 2.05 |
| 5 | 254 | 48 | 5 | 14 | + | − | + | ↑ | 3.04 |
| 6 | 255 | 18 | 6 | 25 | + | + | + | ↔ | 1.64 |
| 7 | 160 | 40 | 5 | 15.5 | + | − | + | ↑ | 3.41 |
| 8 | 210 | 29 | 12 | 12 | − | + | + | ↑ | 5.78 |
| \multicolumn{10}{c}{III, Anaplastic Astrocytoma} |
| 1 | 79 | 32 | 5 | 9.8 | + | − | + | ↑ | 2.35 |
| 2 | 90 | 55 | 12 | 6 | + | − | − | ↑ | 7.70 |
| 3 | 93 | 49 | 3 | 5.5 | + | − | + | ↑ | 18.27 |
| 4 | 140 | 25 | 1 | 7 | + | − | + | ↑ | 3.44 |
| 5 | 172 | 21 | 10 | 8 | + | − | + | ↑ | 5.54 |
| 6 | 184 | 28 | 4 | 9.5 | − | + | + | ↔ | 1.62 |
| 7 | 246 | 30 | 3.5 | 6 | + | − | + | ↑ | 2.10 |
| 8 | 259 | 32 | 12 | 6 | + | − | + | ↑ | 6.34 |
| 9 | 277 | 30 | 3 | 10 | + | − | + | ↑ | 11.42 |
| 10 | 262 | 35 | 6 | 9 | + | − | + | ↑ | 10.21 |
| \multicolumn{10}{c}{II, Diffuse Astrocytoma} |
| 1 | 91 | 33 | 5 | 3 | + | − | + | ↑ | 2.43 |
| 2 | 127 | 32 | 2 | 4 | + | − | + | ↓ | −2.16 * |
| 3 | 248 | 30 | 24 | 1.5 | + | − | + | ↑ | 3.38 |
| 4 | 230 | 27 | 3 | 2 | + | − | − | ↑ | 13.47 |
| 5 | 263 | 43 | 5 | 3 | + | − | + | ↑ | 15.46 |
| 6 | 271 | 13 | 3 | 1.5 | − | − | + | ↑ | 9.78 |
| 7 | 234 | 28 | 11 | 3 | − | − | + | ↑ | 2.29 |

\* - value was derived from semi-quantitative RT-PCR
↑ - up regulated with respect to normal brain
↓ - down regulated with respect to normal brain
↔ - no significant change with respect to normal brain
MIB-LI - MIB-1 Labeling Index, EGFR - Epidermal Growth Factor Receptor, ASCL1 - Achaete-Scute Complex-like 1

Similarly, amplification of epidermal growth factor receptor (EGFR) gene is found in 40% of primary GBMs but it is rare in secondary GBMs (Frederick et al., 2000). These results suggest that the ASCL1 expression could be used differentiate primary from secondary GBMs. Also combined use of ASCL1, p53 and EGFR immunohistochemical staining to differentiate secondary GBMs from Primary GBMs could be considered.

Furthermore, ASCL1 upregulation was found to accompanied by inhibition of notch signaling in grade II diffuse astrocytoma, grade III anaplastic astrocytoma and secondary GBMs, but not in primary GBMs, suggesting that these molecular changes may characterize progressive astrocytoma. We provide below evidence for the regulation of Notch signaling pathway during low grade astrocytoma development from normal astroglial cells and further progression to anaplastic astrocytoma and then to secondary GBM.

During the development of central nervous system (CNS), the neural stem cells, which are common progenitor cells, proliferate and subsequently differentiate into three major cell types of the brain: neurons, astrocytes and oligodendrocytes (Qian et al., 2000). Several molecular mechanisms have been found to be involved in the differentiation of multipotent neural stem cells into different brain cell types. Neurogenic bHLH transcription factors like neurogenin ½ and MASH1, a murine homologue of achaete-scute complex-like 1 (ASCL1), have been shown to inhibit glial differentiation (Furukawa et al., 2000; Nieto et al., 2001; Novitch et al., 2001; Satow et al., 2001; Sun et al., 2001; Zhou et al., 2000). The cytokine leukemia inhibitory factor (LIF) promotes astroglial differentiation through JAK-STAT signaling pathway (Johe et al., 1996; Bonni et al., 1997). Notch signaling has been shown to play a major role in the differentiation of several tissues including nervous tissue in many organisms (Ghysen et al., 1993; Artavanis-Tsakonas et al., 1995, 1999). While the notch signaling inhibits the neuronal and oligodendroglial differentiation, it has recently been reported to instructively drive satellite glial cell differentiation in peripheral neural crest stem cells and to promote astrocyte differentiation in adult hippocampal NSCs (Morrison et al., 2000; Tanigaki et al., 2001).

Since our results show that there is upregulation of ASCL1 in the majority of grade II diffuse astrocytoma, grade III anaplastic astrocytoma and secondary GBMs, we hypothesized that notch signaling may be inhibited during diffuse astrocytoma (grade II) development from astroglial cells, which would further provide suitable environment for progression to anaplastic astrocytoma (grade III) and subsequently to secondary GBM. To test this hypothesis, we analyzed the levels of various notch pathway genes in the same set of samples.

Binding of any of the Notch ligands, which include Delta1, Jagged1, and Jagged2, leads to a complex cleavage and activation of Notch proteins (Artavanis-Tsakonas et al., 1999; Weinmaster, 1997). The released and activated COOH-terminal fragment of Notch translocates to the nucleus where it interacts with the transcription factor CBF1 (RBPjk) to trans-activate target genes including Hairy and enhancer of Split 1 (HES1) (Artavanis-Tsakonas et al., 1999; Weinmaster, 1997). Accordingly, we tested the levels of HES1 in our samples. In our experiments, we found that the transcript levels of the notch target gene HES1, a transcriptional repressor of ASCL1, remain similar to or less than that of normal brain tissue in 52.94% (9/17) of grade II/III astrocytoma (3 out of 7 grade II and 6 out of 10 grade III samples) and 85.7% of (6/7) secondary GBM (FIG. 1B). In contrast to this, the expression of HES1 is increased in most primary GBM samples (75% had more than 1.5 fold transcripts than that of normal; 9/12) (FIG. 1B).

Another member of HES family of genes, HES6, has been shown to functionally antagonize HES1 and relieve positive bHLH factors like ASCL1 from inhibition by HES1 (Bae et al., 2000; Gibert and Simpson, 2003). HES6 actually binds to HES1 and abolishes its ability to repress transcription. In our experiments, We found that the level of HES6 transcripts is increased several fold in majority of samples from grade II diffuse astrocytoma (71.43%; 5/7), grade III anaplastic astrocytoma (66.67%; 6/9) and secondary GBM (71.43%; 5/7) (FIG. 1C). However, the levels of HES6 transcripts did not increase in primary GBMs. The expression levels are in the same range as normal samples in majority of them (75%; 9/12) (FIG. 1C). Thus, the high level of HES6, which is expected to inhibit HES1, gives another explanation for induced expression of ASCL1 in majority of grade II/III astrocytomas and secondary GBMs.

Binding of any of the Notch ligands, which include Delta1, Jagged1, and Jagged2, leads to a complex cleavage and activation of Notch proteins (Artavanis-Tsakonas et al., 1999; Weinmaster, 1997). The released and activated COOH-terminal fragment of Notch translocates to the nucleus where it interacts with the transcription factor CBF1 (RBPjk) to trans-activate target genes including Hairy and enhancer of Split 1 (HES1) (Artavanis-Tsakonas et al., 1999; Weinmaster, 1997). Accordingly, we then analyzed levels of expression of notch ligands Delta1 (Delta-like 1; DLL1) in astrocytoma samples. We found very high levels of Delta1 transcripts in majority of samples analyzed belonging to grade II diffuse astrocytoma (71.43%; 5/7), grade III anaplastic astrocytoma (100% (10/10) and secondary GBMs (85.71% 6/7) (FIG. 1D). However, the Delta1 transcript levels remain unchanged in majority of primary GBMs (91.67%; 11/12) (FIG. 1D). High levels of Delta1 seen in astrocytoma samples over expressing ASCL1 can be explained by the fact that Delta1 is shown to be transcriptionally activated by ASCL1 (Heitzler et al., 1996). In fact the expression of Delta1 appears to be under the control of MASH1 (Post et al., 2000). MASH1 knockout is associated with a total loss of Delta1 expression in the lung (Apelqvist et al., 1999).

Similarly, MASH1 mutants fail to express Delta1 transcripts (Casarosa et al., 1999). Increased levels of notch ligand Delta1 is expected to activate the notch signaling pathway. On the other hand, the presence of uninduced levels of notch target gene HES1 and very high levels of ASCL1 transcripts in these samples are suggestive of inhibition of notch signaling. Because the activity of notch ligands is known to be regulated by glycosylation of notch receptors by fringes (Haltiwanger and Stanley, 2002), we thought regulation of fringe proteins may explain the fact that notch signaling is appears to be inhibited in progressive astrocytoma in spite of the fact that notch ligand Delta 1 is overexpressed in these set of tumors. On analysis, we found no significant change in the expression levels of Lunatic, Radical and Manic fringe in most samples suggesting that fringe molecules may not have any role in inhibiting notch ligands during progressive astrocytoma development (data not shown). It is reported that notch ligands Delta1 and Jagged 1 sequester Notch proteins in the endoreticulum or golgi apparatus of neuronal precursors as intracellular heteromeric complexes and thus reduce the effective dose of Notch signaling (Sakamoto et al., 2002). Thus the over expression of notch ligands is believed to inhibit notch signaling by forming intracellular cell-autonomus ligand:receptor associations rather than activate the notch pathway. Taken together, these results suggest that notch signaling is inhibited early during the development of diffuse astrocytoma and the consequent elevation of ASCL1 may facilitate further progression to anaplastic astrocytoma and later to secondary GBM. Moreover, our data indicate that notch pathway remains activated in primary GBMs and suggest the possibility that notch pathway has no role in the development of primary GBM.

Thus, we present multiple evidences for inhibition of notch signaling pathway during the development of diffuse astrocytoma, which ultimately progresses to secondary GBM. Firstly, the level of ASCL1 transcript is found to be significantly high in majority of grade II/III astrocytoma as well as secondary GBMs. Notch signaling causes transactivation of Hairy and Enhancer of Split (HES) genes, which in turn repress ASCL1 expression through transcriptional mechanisms (Chen et al., 1997). A similar regulation is seen in HES1$^{-/-}$ mice, where the level of ASCL1 is found to be elevated (Ito et al., 2000). Mash1 and Math3, a murine ato homolog have been shown to play a major role in neuronal versus glial fate determination in the CNS and it is possible that downregulation of the Mash1 and Math3 is one of the mechanisms to initiate gliogenesis (Tomita et al., 2000). Thus the increased level of ASCL1 is suggestive of inhibition of notch signaling in progressive astrocytoma. Secondly, the transcript levels of notch target HES 1, an inhibitor of ASCL1 expression, is not induced in majority of grade II/III astrocytomas and secondary GBMs in comparison to normal brain samples. Thirdly, the levels of HES6 transcripts, a dominant negative inhibitor of notch signaling, is increased several fold in majority of grade II/III astrocytomas and secondary GBMs. HES6 is a dominant negative inhibitor of HES1 and it inhibits the function of HES1 by associating with it and abolishing its ability to repress transcription (Bae et al., 2000; Gibert and Simpson, 2003). Finally, we found high levels of Delta1 transcripts in most samples analyzed belonging to grade II/III astrocytoma and secondary GBM. The reason for increased levels of Delta1 can be explained by the fact that Delta1 is shown to be transcriptionally activated by ASCL1 (Heitzler et al., 1996). In fact the expression of Delta1 appears to be under the control of MASH1 (Post et al., 2000). MASH1 knockout is associated with a total loss of Delta1 expression in the lung (Apelqvist et al., 1999). Similarly, MASH1 mutants fail to express Delta1 transcripts (Casarosa et al., 1999). High levels of notch ligand Delta1 is capable of inhibiting notch signaling by forming intracellular cell-autonomus Notch:Delta1 associations (Sakamoto et al., 2002). Thus our data clearly demonstrate the downregulation of notch signaling during progressive astrocytoma development.

It also provides evidence for the fact that inhibition of notch signaling occurs only in the secondary GBM, which is a progressive type, but not in primary GBM, which arises by a de novo process. While ASCL1 levels are upregulated in majority of grade II/III astrocytoma and secondary GBMs, its levels remain unchanged in majority of primary GBMs. The expression levels of other genes associated with notch signaling correlate with the levels of ASCL1 expression.

We also put forward a hypothesis that notch signaling may have tumor suppressor or growth inhibitory role in astroglial cell type. Although, the mammals preferably human Notch1 was originally isolated as an oncogene in acute lymphoblastic leukemia (T-ALL) (Ellisen et al., 1991), this pathway has been shown to have distinctive roles in cancers arising from different tissues. For example, while the Notch signals are oncogenic in pre-T cells (Ellison et al., 1991) and cervical epithelium (Nair et al., 2003), it suppresses tumor development in keratinocytes (Rangarajan et al., 2001; Nicolas et al., 2003). Since notch signaling promotes differentiation of neural stem cells to astroglial cells (Qian et al., 2000), notch expression is likely to be growth inhibitory rather than oncogenic in normal astroglial cells.

Another interesting finding from this study is the upregulation of HES6 in majority of grade II/III astrocytoma and secondary GBMs. HES6 has been found to be over expressed in mammals preferably human primary tumors derived from breast, lung and kidney suggesting that HES6 overexpression may have an oncogenic role (Swearingen et al., 2003). Indeed, HES6 has been located in chromosome 2q37, a region known to be amplified in common adenocarcinomas such as that of the lung, breast, prostate, kidney and ovary (Mitelman et al., 2002). The ability of HES6 to inhibit HES1 activity could be significant in that notch signaling have tumor suppressor role in certain tissues (Rangarajan et al., 2001; Nicolas et al., 2003) and HES1 has been shown to have to play a role of tumor suppressor in mammary gland carcinoma cells (Strom et al., 2000; Muller et al., 2002). Taken together, our data suggest that notch signaling has a tumor suppressor role in astroglial cell type and is inhibited early during the development of low grade astrocytoma, which may provide a suitable environment for further development to anaplastic astrocytoma and then to secondary GBM.

The following examples are given by way of illustration of the present invention and therefore should not be constructed to limit the scope of the present invention.

Example 1

Tissue Collection

Glioma tissue samples were collected from patients, who underwent surgery at Sri Satya Sai Institute of Higher Medical Sciences and Manipal Hospital, Bangalore, India at the time of surgical resection. Control samples comprised nontumorous brain tissue samples (temporal lobe) collected from patients who underwent surgery for intractable epilepsy. A total of thirty-seven glioma samples of different grades were used in this study. Tissues were bisected and one half was snap-frozen in liquid nitrogen and stored at −80° C. until RNA isolation. The other half was fixed in formalin and processed for paraffin sections and these were used to identify the histopathological grade and the type of glioma.

Example 2

RNA Isolation

Total RNA was extracted from the frozen tissue by a combination of the TRIzol method (Invitrogen, USA) and RNeasy Midi kit (Qiagen) according to the manufacturer's instructions. The RNA samples were quantified by measuring the absorbance using a spectrophotometer and visualized on a MOPS-Formaldehyde gel for quantity and quality assurance.

Example 3

Quantitative RT-PCR

The relative quantitation of expression levels of selected genes was carried out using a two-step strategy: in the first step, cDNA was generated from RNA derived from different tissue samples using the High-capacity cDNA archive kit (ABI PRISM); subsequently real-time quantitative PCR was carried out with the cDNA as template using the following gene-specific primer sets and DyNAmo HS SYBR Green qPCR kit (Finnzymes, Finland):

```
ASCL1_Forward:
5'CTCAACTTCAGCGGCTTTGG3',          (SEQ ID NO: 21)

ASCL1_Reverse:
5'GCTCGCCGGTCTCATCCTAC3',          (SEQ ID NO: 22)

HES1_Forward:
5'ATGGAGAAAAATTCCTCGTCCC3',        (SEQ ID NO: 23)

HES1_Reverse:
5'TTCAGAGCATCCAAAATCAGTGT3',       (SEQ ID NO: 24)

HES6_Forward:
5'CCTTGGTGACCAATGCCAG3',           (SEQ ID NO: 25)

HES6_Reverse:
5'CCTGCAAGCCATCCATCAG3',           (SEQ ID NO: 26)

DLL1_Forward:
5'TCCTGATGACCTCGCAACAGA3',         (SEQ ID NO: 27)

DLL1_Reverse:
5'ACACACGAAGCGGTAGGAGT3'.          (SEQ ID NO: 28)
```

The reactions were carried out in the ABI PRISM 7000/7900 (Applied Biosystems) Sequence Detection Systems. Data was analyzed as per the relative quantification model proposed by Pfaffl, which includes efficiency correction (Pfaffl, 2001). All measurements were made in duplicate, and for each qRT-PCR primer set, reaction efficiency estimates were derived from standard curves that were generated using serial dilutions of the pool of cDNA set used for the study. Ribosomal protein L35a was used as internal control as its expression level was found to be unaltered in the previous microarray experiments. Normal brain tissue samples from four different epilepsy patients were used as reference. An increase or decrease in gene expression by 2 fold or more over its mean expression in reference samples was considered significant. For certain samples, data was obtained by semi-quantitative end-point RT-PCR.

Example 4

Immunohistochemistry

Paraffin sections (5 □m) from the tumor and control tissues were collected on chrome-alum coated slides and subjected for immunohistochemistry using the streptavidin-biotin complex/immunoperoxidase method using the following monoclonal (Mab)/polyclonal antibodies: MIB-1 (Ki-67 monoclonal antibody, DAKO, Denmark; 1:50); p53 (DO-1, Oncogene; 1:100); EGFR (Oncogene, 1:25); ASCL1 (Polyclonal, SIGMA; 1:50). Briefly, 5 μm paraffin sections were deparaffinized in xylene, dehydrated in graded alcohol series and rinsed in Tris buffer (50 mM pH 7.6) for 15 minutes. The sections were then microwaved for 15-20 minutes at 700 W in sodium citrate buffer (10 mM pH 6.0) to retrieve antigenicity from paraffin sections. For EGFR staining, the sections were pretreated with 0.05% trypsin at 37° C. for 30 minutes. All sections were further treated with methanol and 3% hydrogen peroxide to block endogenous peroxidase followed by washes with Tris buffer. Milk powder (3%) or bovine serum albumin was used to block background staining for 30 minutes. The sections were then incubated with the primary antibody for 2 hours followed by the linked streptavidin-biotinylated secondary antibody (Universal LSAB, DAKO). 3'3-diaminobenzidine (Sigma) was used as the chromogenic substrate.

Brain tumor samples previously characterized for over expression of p53 and EGFR were used as positive controls. For ASCL1, the tumor sample, which showed marked upregulation by RT-PCR, was taken as the positive control. A negative control slide in which the primary antibody was excluded was used with each batch of slides. For MIB-1 and p53 immunostaining only nuclear staining was regarded as positive where as with EGFR, positive sample showed cytoplasmic and cell surface membrane staining.

For ASCL1 immunostaining, only nuclear staining was considered as positive signal. Tumors were considered ASCL1 positive when more than 5% of tumor cells showed nuclear staining. Regarding p53 and EGFR also, specimens with less than 5% immunopositive tumor cells were scored as negative. The MIB-1 labeling index (LI) was expressed as the percentage of tumor cell nuclei stained, in areas of maximum staining and calculated in at least 1000 tumor cells.

MIB-1 LI was used for accurate grading of astrocytomas. The mean cut-off LI for Grade II astrocytomas was 2.14%±1.042; 7.68%±1.786 for Grade III anaplastic astrocytoma; 19.6%±7.578 for GBM, which more or less corresponded to mean values laid down by the WHO grading scheme (Kleihues et al., 2000).

GBMs were classified as primary or secondary taking into consideration the clinical profile of patients, expression of p53 and EGFR. The mean age of patients with primary GBMs was 50.6 years and mean duration of symptoms was 2.7 months. All tumors showed highly pleomorphic, histomorphological features and evidence of "field necrosis". Uniform staining for EGFR by immunohistochemistry was evident in all cases and five revealed additionally p53 expression. Among secondary GBMs, the mean age of the patients was 33.8 years and mean duration of symptoms was 5.3 months. p53 immunoreactivity was uniformly evident in all cases and two revealed additionally EGFR over-expression. Histological evidence of progression from grades II or III astrocytoma was clearly seen in 5/8 cases.

ADVANTAGES

The main advantages of the present invention are:

(1) The method is useful both before and after clinical symptoms have appeared, and the method can also be applied to monitor the effectiveness of anti-cancer treatments.

(2) It provides a useful method for distinguishing between the two types of Glioblastoma multiforme—the progressive and de novo types.

We claim:

1. A method for identifying the type of glioblastoma multiforme in a human subject, comprising the steps of:
    obtaining a test sample comprising a cell-containing material from the brain of the human subject,
    determining the expression levels of Achaete-scute complex-like 1 gene (ASCL1) having SEQ ID NO: 3, Hairy and Enhancer of Split 1 gene (HES1) having SEQ ID NO: 1, and Hairy and Enhancer of Split 6 gene (HES6) having SEQ ID NO: 5 in the test sample and in a control sample,
    comparing the expression level of the ASCL1, and HES1, and HES6 genes in the test sample with the expression level of the ASCL1, HES1, and HES6 genes in the control sample;
    wherein an increase in the expression level of ASCL1 gene, an increase in the expression level of HES6 gene, and a decrease in the expression level of HES1 gene in the test sample as compared to the control sample indicates the presence of a secondary glioblastoma multiforme.

2. The method of claim 1, wherein the expression levels of said genes are determined by monitoring the expression levels of RNA transcripts of said genes.

3. The method of claim 2, wherein the monitoring is by in situ hybridization or RT-PCR analysis.

4. The method of claim 1, further comprising applying an EGFR marker to the test sample and the control sample, wherein an increase in labeling by the EGFR marker further identifies the secondary glioblastoma multiforme.

5. The method of claim 1, comprising collecting the test sample and the control sample by biopsy, sampling, resecting, removing from in situ, aspirating, receiving, gathering, transporting the tissue sample or a concentrate, sediment, precipitate, supernatant, filtrate, aspirate, or fraction thereof.

6. The method of claim 5, wherein the biopsy is by percutaneous biopsy, laparoscopic biopsy, surgical resection, tissue scrapes and swabs, sampling via stents, catheters, endoscopes, needles, or surgical resection.

* * * * *